US011654202B2

(12) United States Patent
Vinet et al.

(10) Patent No.: US 11,654,202 B2
(45) Date of Patent: May 23, 2023

(54) NANOEMULSION OF IODINATED FATTY ACIDS FOR CT IMAGING

(71) Applicant: UNIVERSITY OF GENEVE, Geneva (CH)

(72) Inventors: Laurent Vinet, Contamine sur Arve (FR); Andrej Babic, Veigy-Foncenex (FR); Eric Allemann, Troinex (CH)

(73) Assignee: UNIVERSITY OF GENEVA, Geneva (CH)

( * ) Notice: Subject to any disclaimer, the term of this patent is extended or adjusted under 35 U.S.C. 154(b) by 0 days.

(21) Appl. No.: 16/637,366

(22) PCT Filed: Jul. 27, 2018

(86) PCT No.: PCT/EP2018/070501
§ 371 (c)(1),
(2) Date: Feb. 7, 2020

(87) PCT Pub. No.: WO2019/030024
PCT Pub. Date: Feb. 14, 2019

(65) Prior Publication Data
US 2021/0330820 A1    Oct. 28, 2021

(30) Foreign Application Priority Data
Aug. 7, 2017   (EP) .................................. 17185185

(51) Int. Cl.
| A61K 49/04 | (2006.01) |
| A61K 9/00 | (2006.01) |
| A61K 49/00 | (2006.01) |
| B82Y 5/00 | (2011.01) |

(52) U.S. Cl.
CPC ........ *A61K 49/0438* (2013.01); *A61K 9/0053* (2013.01); *A61K 49/0004* (2013.01); *A61K 49/0461* (2013.01); *B82Y 5/00* (2013.01)

(58) Field of Classification Search
CPC .............. A61K 49/0438; A61K 9/0053; A61K 49/0004; A61K 49/0461; B82Y 5/00
See application file for complete search history.

(56) References Cited

U.S. PATENT DOCUMENTS

| 5,258,172 A * | 11/1993 | Rubin ................ A61K 49/0495 560/103 |
| 5,861,367 A | 1/1999 | Blanvalet et al. |
| 6,124,357 A * | 9/2000 | Jung .......................... A61P 5/14 514/546 |
| 2005/0079131 A1* | 4/2005 | Lanza ...................... B82Y 5/00 424/1.11 |
| 2008/0319315 A1 | 12/2008 | Kolodny et al. |
| 2015/0045278 A1 | 2/2015 | Beisser et al. |
| 2018/0165808 A1 | 6/2018 | Bagci et al. |

FOREIGN PATENT DOCUMENTS

| CA | 2 315 437 A1 | 2/2001 |
| CN | 101379023 A | 3/2009 |
| CN | 102166365 A | 8/2011 |
| CN | 103626866 A | 3/2014 |
| CN | 105592862 A | 5/2016 |
| EP | 0 294 534 A1 | 12/1988 |
| FR | 2736549 A1 | 1/1997 |
| KR | 10-2012-0107770 A | 10/2012 |
| WO | 2005/100596 A1 | 10/2005 |
| WO | 2008/153928 A2 | 12/2008 |
| WO | 2012/080279 A1 | 6/2012 |
| WO | 2015/127347 A1 | 8/2015 |

OTHER PUBLICATIONS

Lee et al., Atherosclerosis, 2013, 230, p. 177-184. (Year: 2013).*
Hallouard et al.; "Iodinated nano-emulsions as contrast agents for preclinical X-ray imaging: Impact of the free surfactants on the pharmacokinetics;" European Journal of Pharmaceutics and Biopharmaceutics; 2013; pp. 54-62; vol. 83, No. 1.
Lim et al.; "Nanoscaled Iodized Oil Emulsion as a CT Contrast Agent for the Detection of Experimental Liver Tumors in a Rat Model;" Academic Radiology; 2010; pp. 985-991; vol. 17, No. 8.
Zhuang et al.; "Abstract 19281: CT Molecular Imaging of Perivascular Adipose Tissue and Its Linkage to Vascular Disease;" Circulation; 2016; vol. 134, No. Suppl. 1.
Groen et al.; "Absorption and metabolism of lipiodol after oral administration;" American Journal of Medicine, Excerpta Medica, Inc.; 1948; pp. 814-826; vol. 4, No. 6.
Gershon-Cohen et al,; "Oral Hepatosplenography. Some limitations of iodinated, chloriodized and bromiodized oils homogenized with various emulsifiers;" American Journal of Roentgenology 1954; pp. 795-800; vol. 72, No. 3.
Oct. 8, 2018 Search Report issued in International Patent Application No. PCT/EP2018/070501.
Oct. 8, 2018 Written Opinion of the International Searching Authority issued in International Patent Application No. PCT/EP2018/070501.
W.M. Admiraal et al., "Visualisation of brown adipose tissue in humans with 123l-metaiodobenzylguanidine SPECT-CT and 18F-fluorodeoxyglucose PET-CT", Diabetologia, 2012, 55:[Suppl 1], S277-S278, Abstract 677.
L. Zhang et al., "PPAR-? Expression of Hepatocytes after TAE in Liver Cancer", Journal of ali University, 2016, vol. 1, Issue 10, pp. 67-70. (the publication date of the issue is Oct. 15, 2016).
N. Sohn and A.E. Dumont, "Roentgenography of the Thoracic Duct in Man by Oral Administration of Contrast Media.", (28204), v112, 901-903 (1963).
Wang Wan-Sheng et al.. Preliminary study on lung volume reduction by bronchial occlusion with pingyangmycin-ipiodol emulsion. Journal interventional radiology, Jan. 2006, (01): 36-40.

(Continued)

Primary Examiner — Michael G. Hartley
Assistant Examiner — Leah H Schlientz
(74) Attorney, Agent, or Firm — Oliff PLC

(57) ABSTRACT

An iodinated CT contrast agent made of fatty acid derivatives for non-invasive visualisation and quantification of the brown and/or beige adipose tissue (BAT) or for imaging the heart and/or liver of a subject, to be taken orally which is a breakthrough in CT imaging. Image resolution by CT is significantly enhanced compared to PET.

15 Claims, 6 Drawing Sheets

(56) References Cited

OTHER PUBLICATIONS

Zhang Ru-Yan et.al., Percutaneous chemotherapic agents lipiodol emulsion injection for the treatment of pedunculated hepatocellular carcinoma. Contemporary Medicine, vol. 15 (29): 547-549, Oct. 2009.

Y. Zhang et al., "Non-invasive Imaging Methods for Brown Adipose Tissue Detection and Function Evaluation", Intern Med Open Access, 2018;8(6):299.

R.T. Branca et al., "Accurate quantification of brown adipose tissue mass by xenon-enhanced computed tomography", Aug. 16, 2017, PNAS 115 (1) 174-179.

T.S. Hong et al., "Brown adipose tissue 18F-FDG uptake in pediatric PET/CT imaging", Pediatric Radiology, 41, 759-768(2011).

J.D. Steinberg et al., "Factors influencing brown fat activation in FDG PET/CT: a retrospective analysis of 15,000+ cases". The British Journal of Radiology 2017, 90:1075.

C. Cohade et al., "Uptake in Supraclavicular Area Fat ("USA-Fat"): Description on 18F-FDG PET/CT", The Journal of Nuclear Medicine, 44, 170-176 (Feb. 2003).

N. M. Long et al., "Causes and imaging features of false positives and false negatives on 18F-PET/CT in oncologic imaging", Insights Imaging, 2, 679-698 (Sep. 9, 2011).

X. Wang et al., "Positron Emission Tomography/Computed Tomography Potential Pitfalls and Artifacts", Current Problems in Diagnostic Radiology, 38, 156-169 (Aug. 2009).

E.-C. Huang et al., "The Relationship between Brown Adipose Tissue Activity and Neoplastic Status: an 18F-FDG PET/CT Study in the Tropics", Lipids in Health and disease 2011, 10:238.

A. Paulus et al., "Brown adipose tissue and lipid metabolism imaging", Methods, 130, 105-113 (May 19, 2017).

N. Anton et al., "Nano-emulsions and micro-emulsions: clarifications of the critical differences", Pharmaceutical Research, 28, 978-985 (Nov. 6, 2010).

N. Anton et al., "The universality of low-energy nano-emulsification", International Journal of Pharmaceutics, 377, 142-147(May 18, 2009).

J.M. Argilés et al., "The cachexia score (CASCO): a new tool for staging cachectic cancer patients", Journal of Cachexia, Sarcopenia and Muscle, 2, 87-93 (May 15, 2011).

J.M. Argilés et al., "Cancer cachexia: understanding the molecular basis", Nature Reviews Cancer, 14, 754-762 (Nov. 2014).

R. Ballaróet al., "Animal models for cancer cachexia", Current Opinion in Supportive and Palliative Care, 10, 281-287 (2016).

K. Fearon et al., "Definition and classification of cancer cachexia: an international consensus", The Lancet Oncology, 12, 489-495 (May 2011).

A.B. Ferreira et al., "Novel and Highly Efficient SnBr2-Catalyzed Esterification Reactions of Fatty Acids: The Notable Anion Ligand Effect", Catalysis Letters, 143, 1240-1246 (Sep. 4, 2013).

S. Kir et al., "Tumour-derived PTH-related protein triggers adipose tissue browning and cancer cachexia" Nature, 513, 100-104 (Sep. 4, 2014).

S.C. Sampath et al., "Imaging of Brown Adipose Tissue: State of the Art", Radiology, 280, 4-19 (Jul. 2016).

J.A. Vaitkus et al., "The role of adipose tissue in cancer-associated cachexia", Experimental Biology and Medicine, 242, 473-481 (2017).

S. Kir et al., "Cachexia and Brown Fat: A Burning Issue in Cancer", Trends in Cancer, 2, 461-463 (Sep. 2016).

M. Petruzzelli et al., "Mechanisms of metabolic dysfunction in cancer-associated cachexia", Genes and Development, 30, 489-501 (2016).

M. Petruzzelli et al., "A switch from white to brown fat increases energy expenditure in cancer-associated cachexia", Cell Metabolism, 20, 433-447 (Sep. 2, 2014).

N.K. Al-Bulushi et al.," The Medical Case for a Positron Emission Tomography and X-ray Computed Tomography Combined Service in Oman", Sultan Qaboos Univ. Med. J. 13,491-501 (Sep. 1, 2013).

A. Alavi et al., "Positron emission tomography imaging in nonmalignant thoracic disorders", Semin. Nucl. Med. 32, 293-321 (Oct. 4, 2002).

K. Carter et al., "Common causes of false positive F18 FDG PET/CT scans in oncology" Braz. Arch. Biol. Technol. 50, (Sep. 2007).

A.M. Cypess et al. "Identification and Importance of Brown Adipose Tissue in Adult Humans", N. Engl. J. Med. 360, 1509-1517 (Apr. 9, 2009).

B.P. Leitner et al. "Mapping of human brown adipose tissue in lean and obese young men" PNAS 114, 8649-8654 (Jun. 7, 2017).

R. Boellaard et al., "FDG PET/CT: EANM procedure guidelines for tumour imaging: version 2.0" Eur. J. Nucl. Med. Mol. Imaging 42, 328-354 (Dec. 2, 2014).

Y. Miyagawa et al., "Energy Efficiency of Different Emulsification Methods: A Comparative Evaluation" Jpn. J. Food Eng. 16, 71-74 (Mar. 2015).

K.Y. Chen et al., "Brown Adipose Reporting Criteria in Imaging STudies (BARCIST 1.0): Recommendations for Standardized FDG-PET/CT Experiments in Humans", Cell Metabolism, 24, 210-222 (Aug. 9, 2016).

A.M. Cypess et al., "Brown Fat in Humans: Consensus Points and Experimental Guidelines", Cell Metabolism, 20, 108-415 (Sep. 2, 2014).

M. Dong et al., "Role of brown adipose tissue in metabolic syndrome, aging, and cancer cachexia", Frontiers of Medicine, 12, 130-138 (2018).

L. Rui, "Brown and Beige Adipose Tissues in Health and Disease", Comprehensive Physiology, 7,1281-1306 (Oct. 17, 2018).

A.M. Tarola et al., "High performance liquid chromatography determination of fatty acids in drying oils following lipase action", J Chromatogr. Sci, 50,294-300 (Feb. 23, 2012).

R. Leverge et al., "Bioavailability of oral vs intramuscular iodinated oil (Lipiodol UF) in healthy subjects", J. Endocrinol. Invest. 26(2 Suppl):20-6 (2003).

Lipiodol® Ultra-Fluid, extracted from the internet: <https://grls.rosminzdrav.ru/Grls_View_v2.aspx?routingGuid=69f1f1ce-d037-4777-8ba6-e3c571c389b5>.

Center of Disease Control and Prevention, Iodine (last reviewed on Dec. 4, 2014).

European Association for the Study of the Liver (EASL), European Association for the Study of Diabetes (EASD), & European Association for the Study of Obesity (EASO). "EASL-EASD-EASO Clinical Practice Guidelines for the management of non-alcoholic fatty liver disease" J. Hepatol. 64,1388-1402 (2016).

\* cited by examiner

FIG: 1.
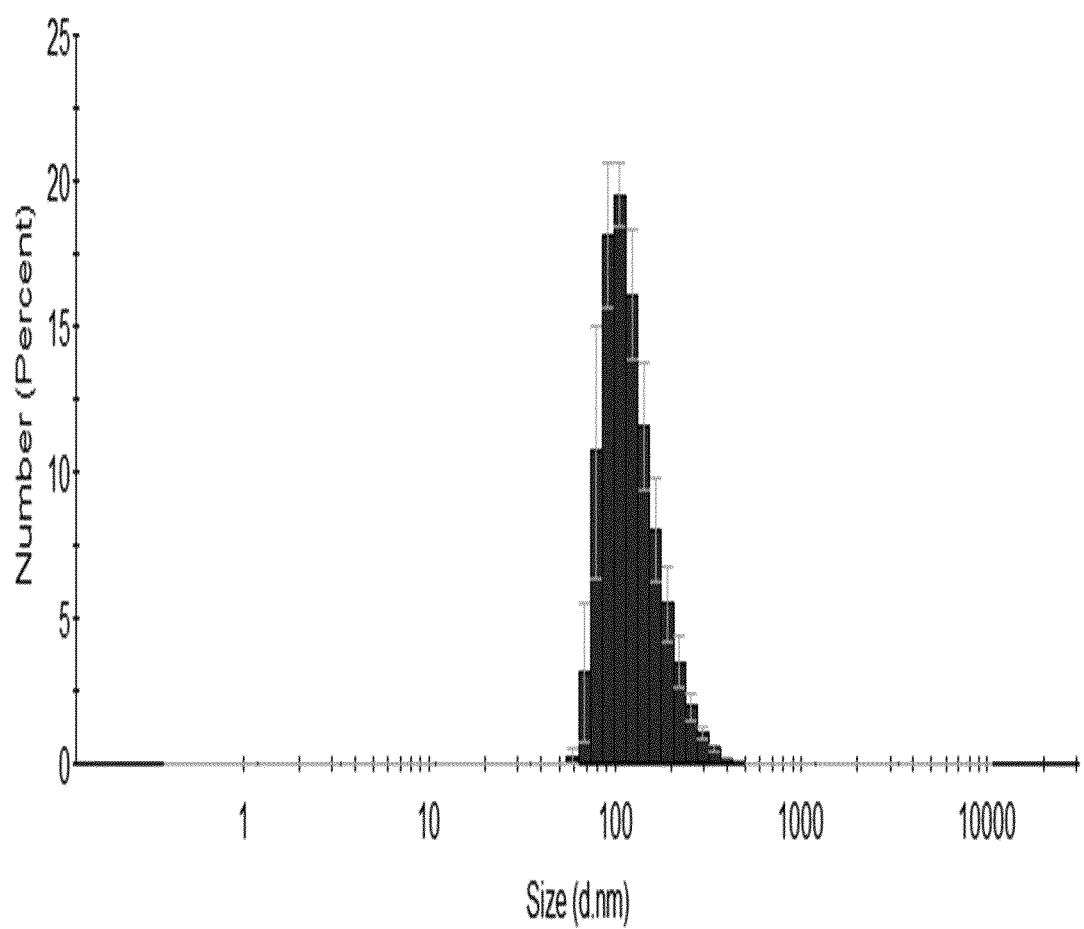

FIG: 2.
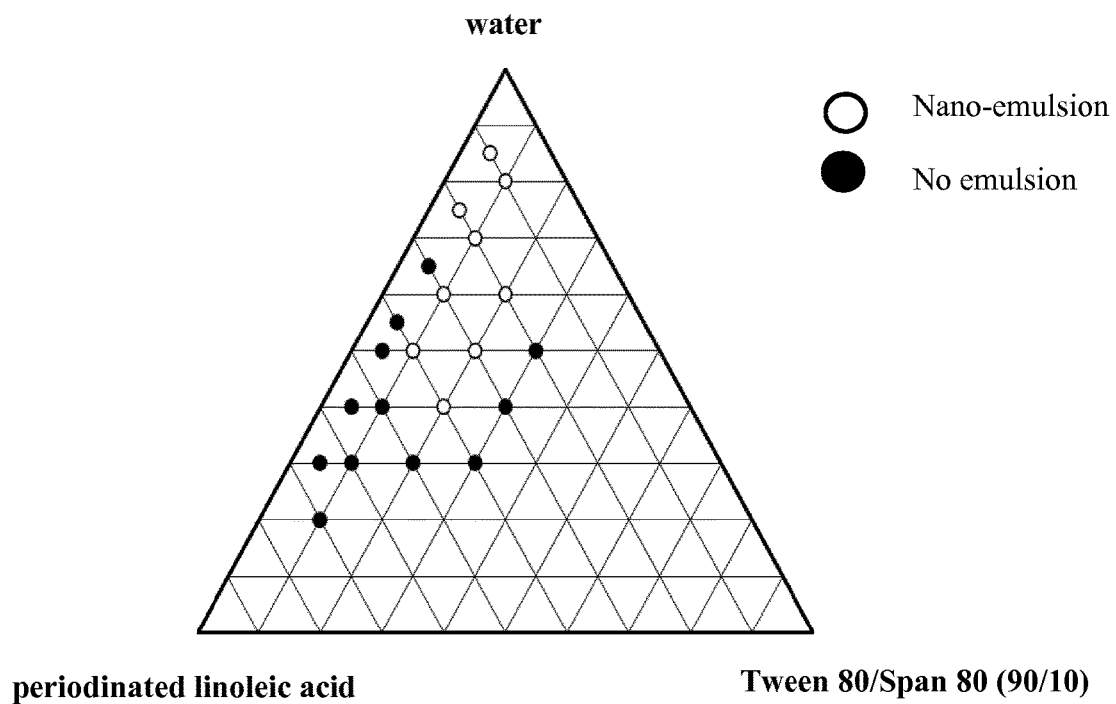

FIG: 3.
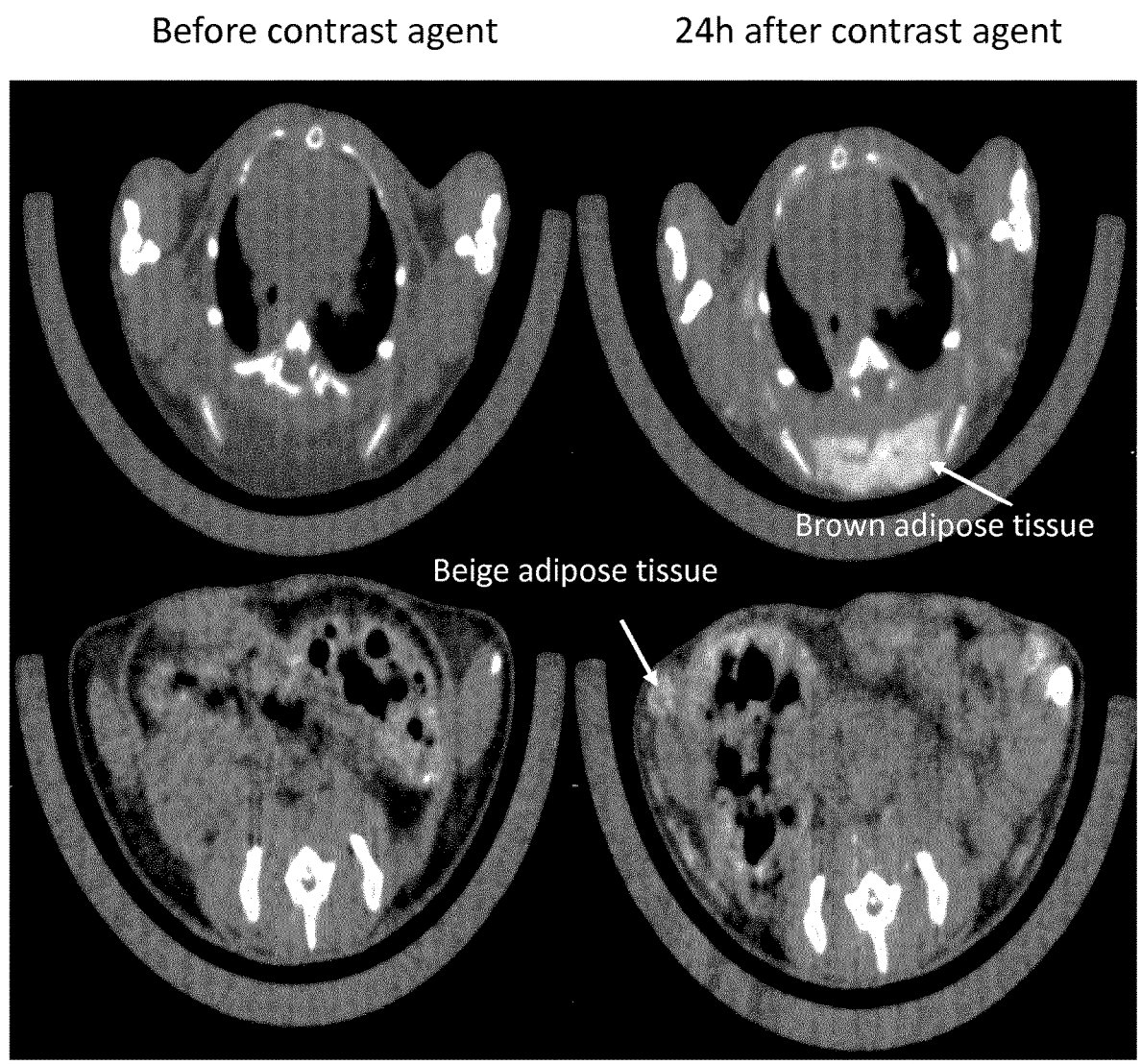

FIG: 4.
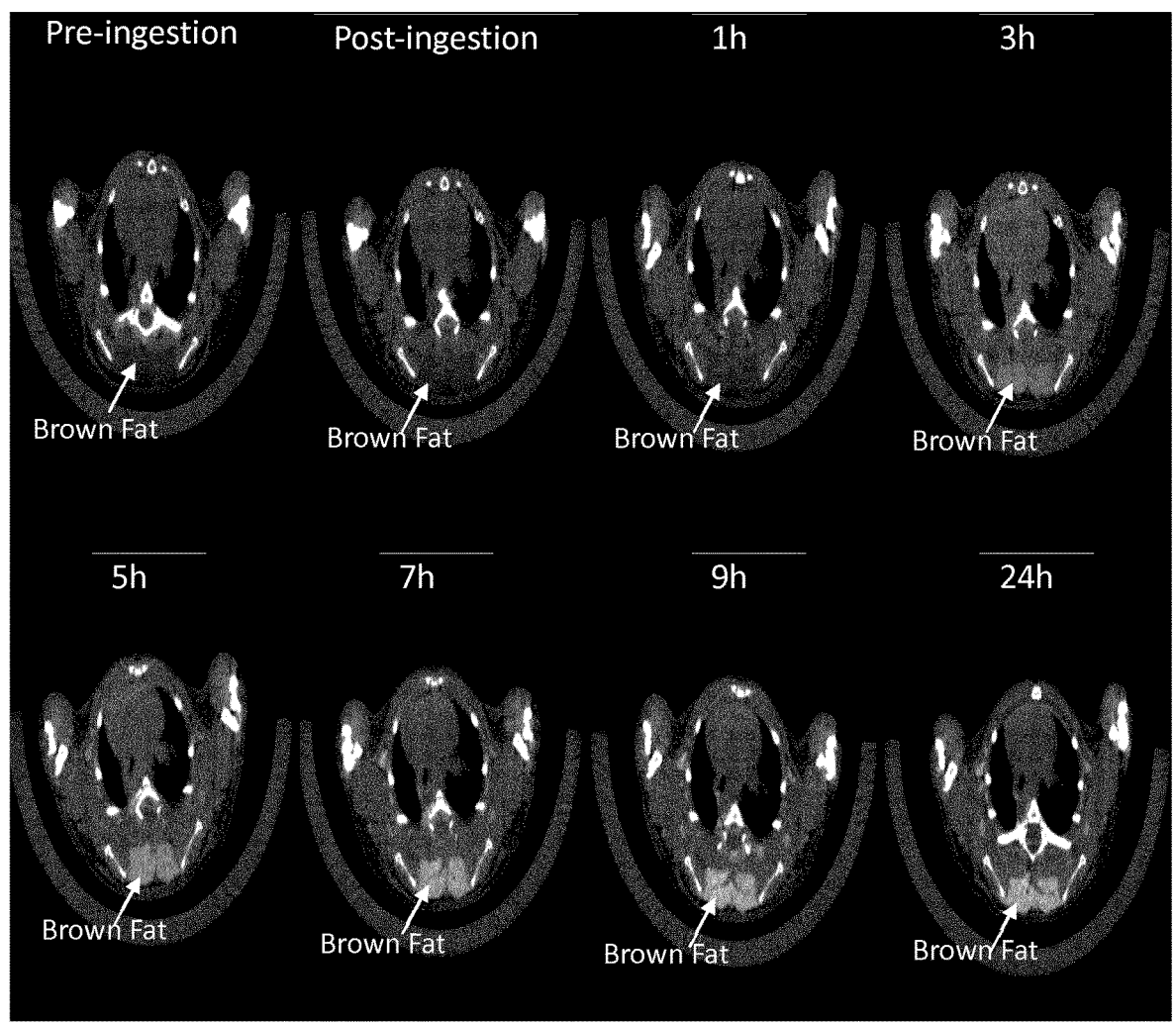

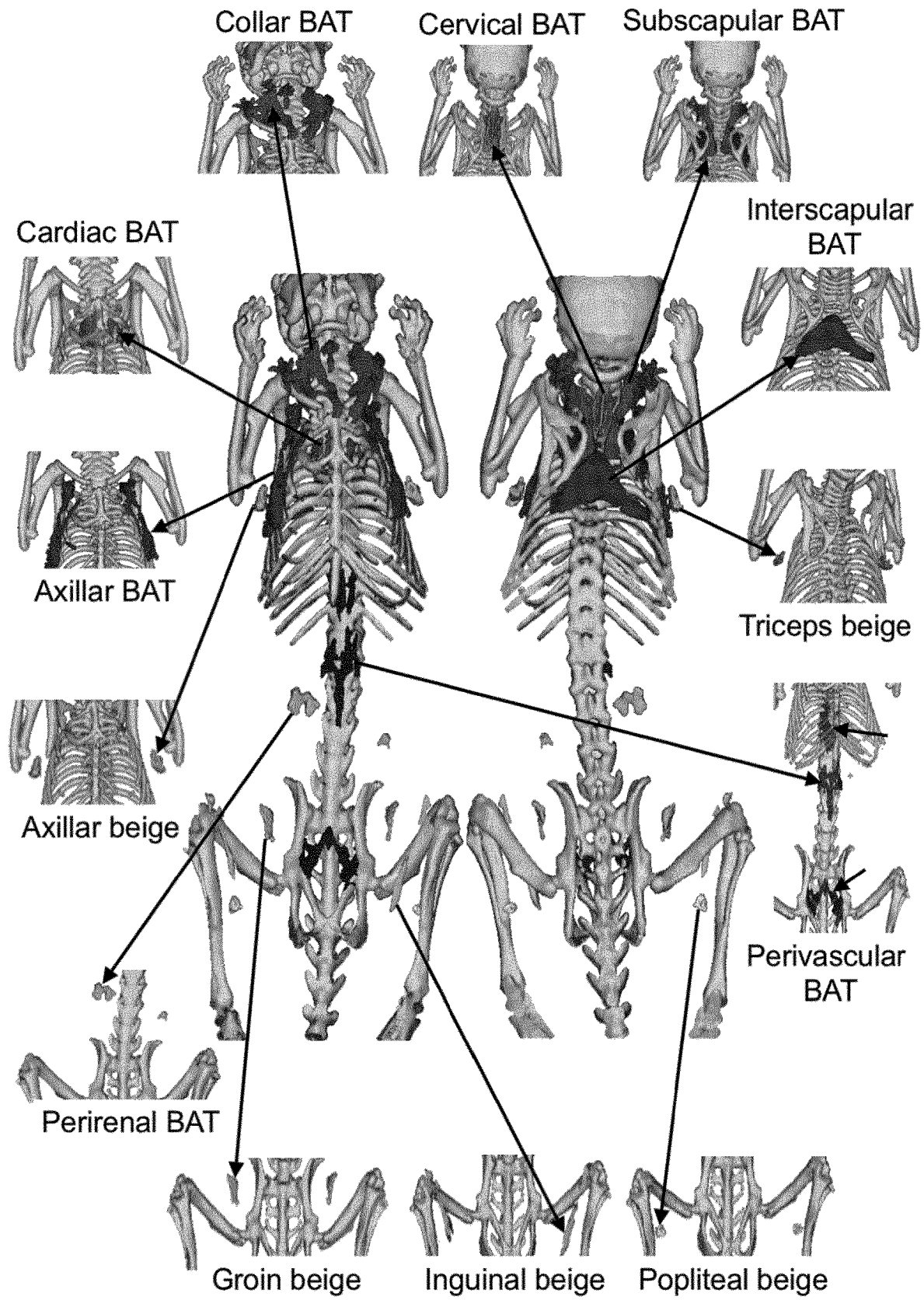
FIG: 5

FIG: 6
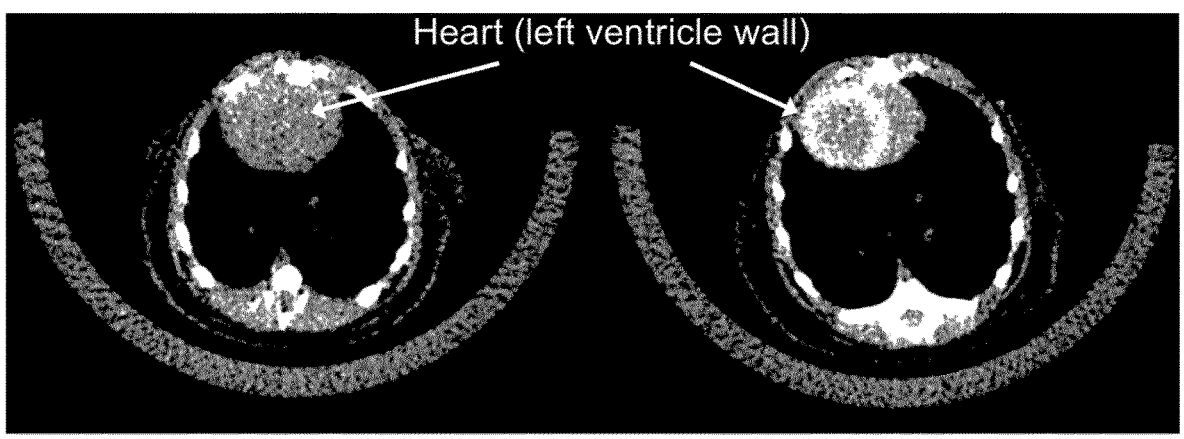
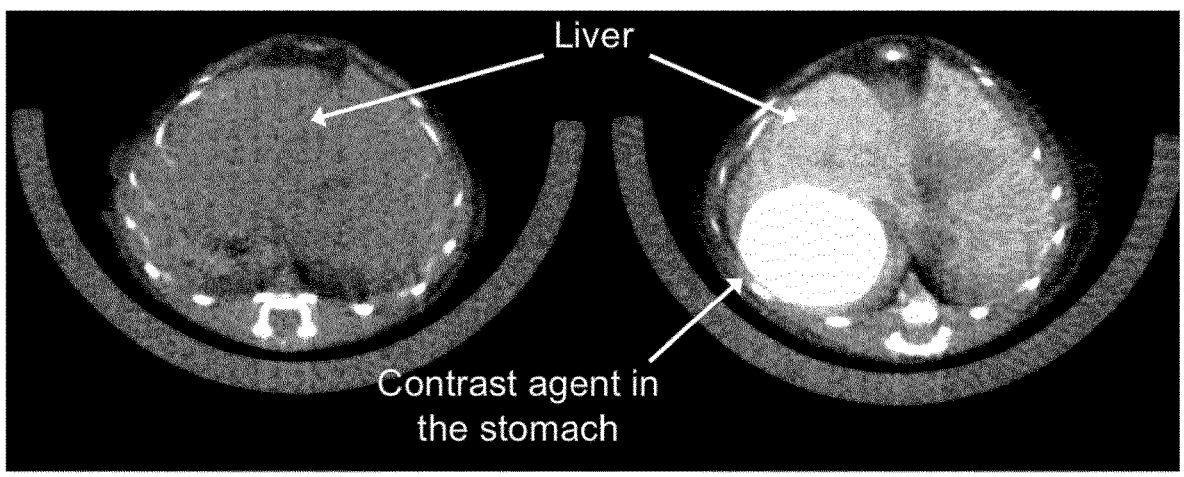

NANOEMULSION OF IODINATED FATTY ACIDS FOR CT IMAGING

FIELD OF THE INVENTION

The invention relates to an iodinated CT contrast agent made of fatty acid derivatives for non-invasive visualisation and quantification of the brown and/or beige adipose tissue or for imaging the heart and/or liver of a subject. Advantageously, this contrast agent is to be taken orally which is a breakthrough in CT imaging. Image resolution by CT is significantly enhanced compared to PET.

BACKGROUND OF THE INVENTION

Obesity is a major health issue. One of its main consequence is type 2 diabetes development. It is mainly due to a high sugar diet and high fat as well as a lack of exercise, and therefore, insufficient energy expenditure. This excess of energy intake is stored mainly as triglycerides in white adipose tissue (WAT). One option to counteract this excess of energy intake could be to force an increase in energy expenditure that could compensate this high caloric intake. Many studies demonstrated that the brown adipose tissue (BAT) or beige adipose tissue dissipates the excess of energy as heat, increasing the energy expenditure. It has also been shown that even if BAT is mainly present in hibernating animals, it is also found in human infants as well as in adult humans.

Brown adipose tissue or beige cells consume glucose and fatty acid, and dissipate them into heat, decreasing on this way fatty acid circulation[1], and improving glucose metabolism. In the BAT, a protein named the uncoupling protein one (UCP1) is responsible for this energy dissipation as heat. This protein, present in the inner membrane of the mitochondria, uncouples the respiratory chain, decreasing the production of ATP and dissipating the excess of protons gradient as heat. More recently, adipocytes expressing UCP1 have been shown to be present in the white adipose tissue (WAT) and have been named beige or brite adipocytes[1]. Unfortunately, their role and activity remain poorly known, as well as their part in the metabolism in comparison with the brown adipocytes. This question is of great interest as adult humans seem to have very little BAT whereas there are many inducible beige adipocytes in the sub cutaneous WAT[2].

The development and evaluation of WAT browning agents is taking more and more importance. Therefore, methods to assess in vivo and over the time, the effect of these agents on the presence and function of beige and brown adipocytes becomes crucial. [18]FDG-PET is the dominant imaging modality to assess brown adipose tissue but suffers from several limitations[1]. Although glucose is taken up upon BAT activation, the main substrate is believed to be fatty acids[3]. Therefore, glucose uptake measured by [18]FDG-PET could underestimate BAT activity under physiologically significant conditions such as mild cold exposure. Furthermore, some pathological conditions such as insulin resistance in type 2 diabetes (T2D) could mitigate or bias the quantification of the BAT activity with [18]FDG-PET. In addition, fatty acids tracer for PET, such as $^{18}$F-fluoro-thiaheptadecanoic acid (18FTHA)[4] was already tested for BAT imaging but seems to offer low signal in human.

Lipiodol (labeled Ethiodol in the USA), also known as ethiodized oil, is a poppyseed oil used by injection as a radio-opaque contrast agent that is used to outline structures in radiological investigations. It is also used in chemoembolization applications as a contrast agent in follow-up imaging. Lipiodol is also used in lymphangiography, the imaging of the lymphatic system. It has an additional use in gastric variceal obliteration as a dilutant that does not affect polymerization of cyanoacrylate.

Recently there has been an increasing interest in the use of Lipiodol as a therapeutic agent in the management of unexplained infertility, using a procedure called Lipiodol flushing. There have been a small number of studies that suggest that flushing the media through the tubes gives a short-term rise in fecundity in patients with unexplained infertility. A systematic review has suggested a significant increase in fertility, especially in those women who have endometriosis when using Lipiodol flushing.

Historically Lipiodol was often used as a contrast medium at hysterosalpingography (HSG: a procedure to determine tubal patency, used in the investigation of subfertility). It became less commonly utilised in the 1960s to 1980s because the more modern water-soluble media give images that are easier to interpret. There is also an important safety issue with Lipiodol in that intravasation (leakage) of the fluid into the venous system has caused complications in the past. Ethiodized oil is composed of iodine combined with ethyl esters of fatty acids of poppyseed oil, primarily as ethyl monoiodostearate and ethyl diiodostearate. The precise structure is not known.

Lipiodol can also be used orally for the prevention of iodine deficiency disorders such as goiter, growth and mental retardation, or cretinism. Lipiodol and other iodized oils have also been successfully employed to prevent iodine deficiency in pregnant women where dietary salt iodization has not yet successfully been established.

In Francois Hallouard et al. "Iodinated nano-emulsions as contrast agents for preclinical X-ray imaging: Impact of the free surfactants on the pharmacokinetics" European Journal of Pharmaceutics and Biopharmaceutics, vol. 83, no. 1, 1 Jan. 2013, pp 54-62, XP055443136, important aspects in the design of contrast agents for X-ray preclinical imaging are presented. The first one is a simple formulation of long circulating contrast agents, formulated from a commercial iodinated oil, and resulting in CT contrast agents containing more than twice the iodine concentration commercial contrast agents. The second point is a methodological aspect, utilizing tangential filtration for reducing the residual surfactants in the bulk phase and serving as well for concentrating droplets (and iodine) in the suspension. The last point is a more general aspect regarding the influence of the free surfactant on the pharmacokinetics and biodistribution of the nano-emulsion droplets on mice.

Besides, Soo-Jeong Lim et al. "Nanoscaled Iodized Oil Emulsion as a CT Contrast Agent for the Detection of Experimental Liver Tumors in a Rat Model", Academic Radiology, Elsevier, Volume 17, Issue 8, 1 Aug. 2010, Pages 985-991, XP027119104 discloses an iodized oil emulsion for computed tomography (CT) imaging of experimental hepatic tumors in rat models. The hepatic enhancement achieved by the iodized oil emulsion is reticuloendothelial system-specific with the property of blood pool enhancement and longer lasting than that achievable with the current water soluble agents. Thus, this agent may offer significant advantages for diagnosis of hepatic metastases.

EP 0 294534 A1 (KABIVITRUM AB [SE]) relates to an emulsion for use as an X-ray contrast agent and containing one or more iodinated lipids emulsified in an aqueous phase. The emulsion contains one or more amino acids, fatty acids or their salts, fat-soluble vitamins and/or urea for increasing its stability. Furthermore, the emulsion may contain one or more pharmacologically acceptable oils or fats. By the stability-increasing agents, it has been possible to prepare emulsions of iodinated lipids which can be sterilized in an autoclave and be stored for a long time without the emulsion breaking.

Zhuang Zhen W et al. "CT Molecular Imaging of Perivascular Adipose Tissue and Its Linkage to Vascular Disease" CIRCULATION, vol. 134, no. Suppl. 1, 11 Nov. 2016, XP002777573, discloses that perivascular adipose tissue (PVAT) surrounds the major arteries and regulates endothelial functioning. Healthy PVAT has the brown adipose tissue (BAT) phenotype histologically, and possesses anti-inflammation and vasorelaxant characteristics, which are not observed in obesity. The hypothesis of this study is that molecular imaging using micro-computed tomography (microCT) combined with an iodinated fatty acid can detect healthy murine PVAT in rest and identify dynamic changes of PVAT after pharmacological or physiological interventions.

Nevertheless, there is a lack of specific CT contrast agents for imaging of brown and beige tissue today which means that it is difficult to detect, image and monitor this tissue in vivo. Despite the fact that some areas on a CT scan can be defined as brown adipose tissue without the use of CT contrast agent, a non-expert will appreciate a considerable advance in detection limits, quantification and quality of brown or beige adipose tissue with the use of new generation of CT contrast agents. It is especially true when considering beige adipocytes that are scattered within the white adipose tissue and impossible to visualize without contrast agent.

Besides, among the various routes of administration, oral administration is considered to be the most acceptable and economical method. Injections are usually administered in a hospital setting as it requires an experienced professional to administer the contrast agent, especially intravenous (IV) infusions. Typically, a patient will be asked to sign an "informed consent form" prior to having an IV CT exam which uses iodine contrast. This form will outline the potential side effects of the iodine. Serious reactions, may include breathing difficulty, swelling of the throat, or swelling of other parts of the body. These reactions can be more serious if not treated immediately. On the contrary, oral formulations are easier to administer, safe and achieve desired concentrations, thus making the peroral (PO) route an ideal choice.

Oral contrast is often used to enhance CT images of the gastrointestinal tract. There are two different types of substances used for oral CT contrast. The first, barium sulfate, is the most common oral contrast agent used in CT. The second type of contrast agent is sometimes used as a substitute for barium and is called Gastrografin. Patients usually need to drink at least 1000 to 1500 cc to sufficiently fill the stomach and intestines with oral contrast. The contrast agent of the invention might not be well suited for gastrointestinal tract imaging because it will be absorbed similarly as dietary fat by intestines. After absorption into the blood compartment it will be preferentially taken up by several organs described below. On the contrary, barium sulfate or iodinated contrast agent for gastrointestinal tract examination are used to image the intestines without any goal to image internal (parenteral) organs.

Unfortunately, there is currently no CT contrast agent that can be taken orally to visualise and quantify fat metabolism of the brown and beige adipose tissue or for imaging the heart or liver of a subject. It is thus an object of the invention to overcome these significant technical problems by providing a peroral iodinated CT contrast agent.

BRIEF DESCRIPTION OF THE INVENTION

One of the objects of the present invention is to provide a method of in vivo imaging with Computed Tomography (CT) parenteral organs comprising administering orally in a subject a contrast agent comprising a biocompatible nano-emulsion of iodinated fatty acids having 4 to 24 carbon atoms and/or esters and/or salts and/or mixtures thereof according to general formula I:

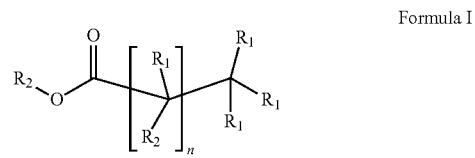

Formula I wherein n=2-22;
$R_1$ is H or I, with the provisions that the number of iodine atoms is 1 to 6, and that the iodine atoms are neither geminal nor vicinal;
and where $R_2$ is H, unsaturated or saturated, linear or branched alkyls, alkoxyalkyl, hydroxyalkoxyalkyl, polyhydroxyalkyl, hydroxy poly alkyleneoxyalkyl.

Surprisingly said CT contrast agent is adapted for an oral use (i.e. peroral).

Another object of the present invention is to provide a method of in vivo imaging with Computed Tomography brown and/or beige adipose tissue (BAT) in a subject, comprising administering orally a contrast agent comprising a biocompatible nano-emulsion of iodinated fatty acids having 4 to 24 carbon atoms and/or esters and/or salts and/or mixtures thereof according to general formula I (as defined above).

A further object of the invention is to provide a method of in vivo imaging with Computed Tomography the heart or the liver in a subject, comprising administering orally a contrast agent comprising a biocompatible nano-emulsion of iodinated fatty acids having 4 to 24 carbon atoms and/or esters and/or salts and/or mixtures thereof according to general formula I as described above.

Other objects and advantages of the invention will become apparent to those skilled in the art from a review of the ensuing detailed description, which proceeds with reference to the following illustrative drawings, and the attendant claims.

BRIEF DESCRIPTION OF THE FIGURES

FIG. 1: Shows the size distribution of the nano-emulsion prepared with diiodostearic acid, excipients (Tween 80, Span 80) in water. The average size of the oil droplets was around 100 nm determined by dynamic light scattering.

FIG. 2: Illustrates the ternary nano-emulsion plot with diiodostearic acid, excipients (Tween 80, Span 80) and water. The white dots represent nano-emulsions and the black dots represent absence of nano-emulsions or phase separation.

FIG. 3: Shows a CT scan axial view of a mouse before and 24 h after the oral administration of the nano-emulsion.

FIG. 4: Shows the brown adipose tissue enhancement kinetic before and after the oral ingestion of the nano-emulsion.

FIG. 5: Shows 3D representation of brown and beige adipose tissue in a mouse housed at 6 degrees and the detailed description of each brown and beige depots in the mouse body.

FIG. 6: Shows CT scan axial views of a mouse without and 7 h after the oral administration of the nano-emulsion revealing the enhancement of the cardiac muscle (FIG. 6a) and the liver (FIG. 6b).

DETAILED DESCRIPTION OF THE INVENTION

Computed tomography (CT) contrast agents have seen only incremental improvements over the last 20 years. Nevertheless, Applicants have developed an iodinated CT contrast agent made of fatty acid derivatives for non-invasive visualisation and quantification of the brown and beige adipose tissue (BAT). Advantageously, this contrast agent is to be taken perorally which is a breakthrough in CT imaging. Currently there is no CT contrast agent that can be taken orally to visualise and quantify fat metabolism of the brown adipose tissue or for imaging the heart and liver of a subject. Image resolution by CT is significantly enhanced compared to PET.

The oral route is commonly used for administration of iodinated oils in order to treat goiter or in the case of a nuclear accident but this route of administration has never been described as a mean of delivering a contrast agent for CT imaging of parenteral organs. In addition, experiments performed by Applicants showed toxicity after iv (intravenous) injection of the iodinated fatty acids and a perfect and fast absorption with no adverse effect after oral administration.

Using this iodinated CT contrast agent at preclinical or clinical level also allows for the evaluation and monitoring of treatments aiming at increasing the activity of the brown and beige adipose tissue, which is a promising approach to treat diabetes and obesity.

Radioactive $^{18}$F-deoxyglucose-PET is the dominant imaging modality to non-invasively assess BAT but it suffers from several limitations. Glucose uptake measured by $^{18}$FDG-PET could underestimate BAT activity under physiologically significant conditions such as mild cold. Furthermore, some pathological conditions such as insulin resistance in type 2 diabetes could mitigate or bias the quantification of the BAT activity with $^{18}$FDG-PET. Compared to PET, image resolution by CT is significantly better, the radiation dose could be reduced and CT technology is more widely available in the clinics worldwide.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of a diagnosis or a subject with a diagnosed disease or disorder. However, in other embodiments, the subject can be a healthy subject. The term does not denote a particular age or sex. Thus, adult and newborn subjects, whether male or female, are intended to be covered.

The term "emulsion" is usually interpreted to refer to a colloidal system of droplets of one liquid dispersed in another liquid with which it is immiscible; such definition would only embrace systems of water and liquid fatty acids or its derivatives and not dispersions of solid fatty acids or their derivatives.

The term "nano-emulsion" is used herein to embrace colloidal systems of solid or liquid fatty acids or their derivatives in water; the precise physical form of the disperse particles of oil phase is not certain but the particles are probably solid, semi-solid or liquid. The average size of the nano-emulsion will be in the nm range, preferably below 1000 nm (see FIG. 1).

The terms "parenteral organs" in the context of the invention refer to imaging organs elsewhere in the body than the mouth and/or the alimentary canal (i.e. gastrointestinal tract). Parenteral organs represent organs situated or occurring outside the intestine, accordingly it refers to the final location of the organs and not the route of administration. This definition refers to organs (also referred herein as "internal organs") located inside the body but outside the intestine or digestive tract.

The term "iodinated fatty acids" used in carrying the invention into effect can be straight or branched, saturated aliphatic carboxylic acids containing at least 4 and preferably not more than 24 carbon atoms in the molecule, such as iodinated oleic, linoleic, linolenic, steridonic, arachidonic, elaindic, gondoic, erucic, docosatetraenoic, eicosapentaenoic or docosahexaenoic acid and similar, used alone or administered with each other or with small amounts of other fatty acids. They contain maximum number of iodine atoms as a consequence of hydroiodination reaction of natural or synthetic fatty acid alkene double bonds. The invention also encompasses "periodinated" fatty acids and/or esters thereof, this term refers to iodinated fatty acids and/or esters that possess the maximum possible amount of iodine atoms within their chemical structures. According to a particular embodiment of the invention periodinated fatty acids and/or esters thereof are preferred.

According to the present invention, pharmaceutically acceptable salts of the iodinated fatty acids compound of the invention are also encompassed.

As used herein, the phrase "pharmaceutically acceptable salt" (also referred herein as "salt") refers to a salt that retains the biological effectiveness of the free acids of the iodinated fatty acids compound of the invention and that is not biologically or otherwise undesirable. The pharmaceutically acceptable salts of the iodinated fatty acids compound of general formula (I) are acid addition salts with pharmaceutically acceptable acids.

A desired salt may be prepared by any suitable method known in the art, including treatment of the free acid with an inorganic base, such as lithium hydroxide, sodium hydroxide, potassium hydroxide, calcium hydroxide, magnesium hydroxide, zinc hydroxide, or organic base, such as ammonium hydroxide, methylamine, dimethylamine, trimethylamine, diethylamine, trimethylamine, morpholine, piperazine, L-arginine, 4-phenyl-cyclohexylamine, benethamine, benzathine, betaine, hydrabamine, 4-(2-hydroxyethyl) morpholine, 1-(2-hydroxyethyl)-pyrrolidine, 1-(2-hydroxyethyl) piperazine, N-methylglucamine, N,N,N-trimethyl ethanolamine hydroxide, tromethamine and the like.

Generally, the salts are prepared by charging the free acid into an organic solvent such as a lower alkanol, symmetrical or asymmetrical ethers containing 2 to 10 carbon atoms, an alkyl ester, or mixtures thereof, and then treated with stoichiometric amounts or with an excess of the desired salt forming inorganic or organic base to form the corresponding salt. The salt is recovered by standard recovery techniques, for example, by evaporation of the solution, or by filtration of the desired salt from the mixture, or it can be precipitated by the addition of a solvent in which the salt is insoluble and recovered there from.

Examples of suitable inorganic and organic solvents for performing the various reactions include any inorganic or organic solvent that does not adversely affect the reactants or the resulting product, including halogenated solvents such as methylene chloride, chloroform, ether solvents such as diethyl ether, and other solvents such as tetrahydrofuran, dioxane, diglyme, cyclooctane, benzene or toluene, heptane, cyclohexane, aliphatic as well as cycloaliphatic and aromatic hydrocarbon solvents, water, aqueous solutions, mixed organic and inorganic solutions, ethyl acetate, propyl acetate and mixtures thereof.

Preferred inorganic cations comprised in the salts are lithium, sodium, potassium, rubidium, ammonium, calcium, magnesium, zinc and manganese.

In chemistry, the term "geminal" used herein refers to the relationship between two atoms or functional groups that are attached to the same atom.

The related term "vicinal" refers to the relationship between two functional groups that are attached to adjacent atoms. Currently it is almost impossible to synthetize iodinated fatty acids and/or esters thereof having iodine atoms attached to adjacent carbon atoms (i.e. vicinal). Because of steric hindrance, those molecules are unstable and cannot be used for the purpose of the present invention. However it might be possible that in the future, the skilled in the art would find a technical solution to this problem. Thus in case stable iodinated fatty acids and/or esters thereof having iodine atoms in vicinal positions are provided, it is believed that those compounds will also be suitable in solving the technical problem of the present invention.

As used herein, the term "alkyl" includes any long or short chain, straight-chained or branched aliphatic saturated or unsaturated hydrocarbon group. The unsaturated alkyl groups may be mono- or polyunsaturated and include both alkenyl and alkynyl groups. Such groups may contain up to 40 carbon atoms. However, alkyl groups containing up to 10 eg. 8, more preferably up to 6, and especially preferably up to 4 carbon atoms are preferred.

The term "alkoxyl" represents —O-alkyl. An example of an alkoxyl is a C1-C6 alkoxyl, which represents a straight or branched alkyl chain having from one to six carbon atoms attached to an oxygen atom. Exemplary C1-C6 alkoxyl groups include methoxyl, ethoxyl, propoxyl, isopropoxyl, butoxyl, sec-butoxyl, t-butoxyl, pentoxyl, hexoxyl, and the like. C1-C6 alkoxyl includes within its definition a C1-C4 alkoxyl.

The term "aryl" as used herein refers to a carbocyclic or heterocyclic, aromatic, 5-14 membered monocyclic or polycyclic ring. Exemplary aryls include phenyl, naphthyl, anthryl, phenanthryl, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

In organic chemistry, a "saturated" compound is a chemical compound that has a chain of carbon atoms linked together by single bonds. Alkanes are saturated hydrocarbons. An "unsaturated" compound is a chemical compound that contains carbon-carbon double bonds or triple bonds, such as those found in alkenes or alkynes, respectively. Saturated and unsaturated compounds need not consist only of a carbon atom chain. They can form straight chain, branched chain, or ring arrangements. They can have functional groups, as well. It is in this sense that fatty acids are classified as saturated or unsaturated. The amount of unsaturation of a fatty acid can be determined by finding its iodine number.

Unsaturated compounds are those in which addition reaction can be obtained. In a chain of carbons, such as a fatty acid, a double or triple bond will cause a kink in the chain. These kinks have macro-structural implications. Unsaturated fats tend to be liquid at room temperature, rather than solid, as the kinks in the chain prevent the molecules from packing closely together to form a solid, these fats are called oils.

The term "polyhydroxy" or polyhydric refers to a chemical compound containing two or more hydroxyl groups per molecule.

It is an object of the present invention to provide for a method of in vivo imaging with Computed Tomography (CT) parenteral organs comprising administering orally in a subject a contrast agent comprising a biocompatible nanoemulsion of iodinated fatty acids having 4 to 24 carbon atoms and/or esters and/or salts and/or mixtures thereof according to general formula I:

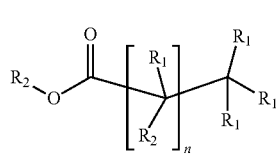

Formula I wherein n=2-22;

$R_1$ is H or I, with the provisions that the number of iodine atoms is 1 to 6, and that the iodine atoms are neither geminal nor vicinal;

and where $R_2$ is H, unsaturated or saturated, linear or branched alkyls, alkoxyalkyl, hydroxyalkoxyalkyl, polyhydroxyalkyl, hydroxy poly alkyleneoxyalkyl.

Surprisingly said CT contrast agent is adapted for an oral use (i.e. peroral).

Preferably, $R_2$ group may be mono or poly-substituted. Suitable $R_2$ groups can include but are not limited to a set of alkyl substituents such as methyl, ethyl, propyl, isopropyl, butyl, isobutyl, t-butyl, cyclopropylmethyl, pentyl, isopentyl, hexyl, isohexyl, heptly, isoheptyl, octyl, isooctyl, 2-propenyl, allyl, crotyl, 1-butenyl, 2-butenyl, butadienyl, ethynyl, 1-propynyl, 2-propynyl, 1-butynyl, 2-butynyl, 3-butynyl and propagyl, cyclopentyl, cyclohexyl, cycloheptyl, admantyl; aryls substituents such as phenyl, naphthyl, anisyl, toluyl, xylenyl, aryloxy, aralkyl, aralkyloxy, heteroaryl groups (pyrimidine, morpholine, piperazine, piperidine, thiophene), 1-cyclohexylpropyl, or haloalkyls substituents such as fluoromethyl, 1-fluoroethyl, 2-fluoroethyl, difluoromethyl, trifluoromethyl and pentafluoroethyl, chlorodimethyl, chloromethyl, 2-chloroethyl, 2,4-dichlorophenyl, 1,1,2,2-tetrachloroethyl, 1-chlorobutyl, and 4-chlorobenzyl.

It can include substituted alkyl groups such as 9-fluorenylmethyl, methoxyethoxymethyl, tetrahydropyranyl, pivalyloxymethyl, phenylacetoxymethyl, phenacyl and substituted phenacyl such as p-bromophenacyl, p-methoxyphenacyl, and also t-butyl, 3-methyl-3-pentyl, cyclopentyl, cycohexyl, allyl, 3-buten-1-yl, cinnamyl, oxazole, and 2-alkyl-1,3-oxazoline. It can also include alkylaryl such as benzyl, substituted benzyl such as triphenylmethyl, p-methoxybenzyl, 4-picolyl, dipohenylmethyl phenylethyl, substituted phenylethyl, but also alkoxyalkyl such as methoxymethyl, ethoxymethyl, propoxymethyl, butoxymethyl, methoxyethyl, ethoxyethyl, propoxyethyl, isopropoxyethyl, butoxyethyl, isobutoxyethyl, hydroxyalkoxyalkyl such as hydroxymethoxymethyl, 2-hydroxyethoxymethyl, 3-hydroxypropoxymethyl, 4-hydroxybuthoxymethyl, hydroxymethoxyethyl, hydroxymethoxypropyl hydroxymethoxybutyl, hydroxymethoxypentyl, hydroxymethoxyhexyl, polyhydroxyalkyl, and hydroxypolyalkyleneoxyalkyl.

The iodinated fatty acids having 4 to 24 carbon atoms and/or esters and/or salts and/or mixtures thereof according to general formula I comprises the following sub-formulae A, B, and C depending on the starting material used.

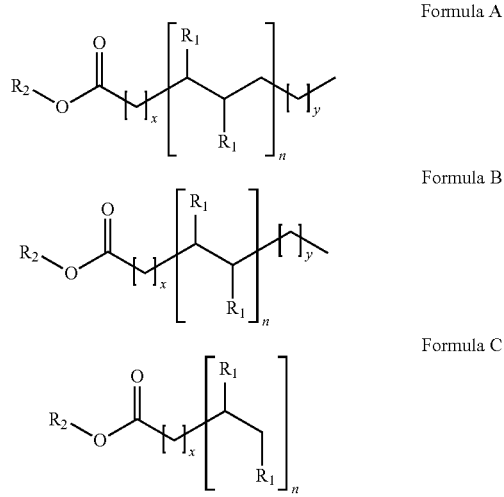

Formula A

Formula B

Formula C where n is an integer of 1-6, and x, y are carbon atoms in which x=0-20 and y=0-20 and x+y≤20 with the provision that the total number of carbon atoms in Formulae A, B or C respectively is 24;

and where $R_2$ group may be mono or poly-substituted.

Thus suitable $R_2$ groups include for example unsubstituted alkyl, such as methyl, ethyl, propyl, isopropyl, butyl, isobutyl, pentyl, isopentyl, hexyl, isohexyl, heptyl, isoheptyl, octyl, isooctyl and similar but also substituted alkyl groups such as 9-fluorenylmethyl, methoxyethoxymethyl, tetrahydropyranyl, pivalyloxymethyl, phenylacetoxymethyl, phenacyl and substituted phenacyl such as p-bromophenacyl, p-methoxyphenacyl, and also t-butyl, 3-methyl-3-pentyl, cyclopentyl, cycohexyl, allyl, 3-buten-1yl, cinnamyl, oxazole, 2-alkyl-1,3-oxazoline and similar. It also includes alkylaryl such as benzyl, substituted benzyl such as triphenylmethyl, p-methoxybenzyl, 4-picolyl, dipohenylmethyl phenylethyl, substituted phenylethyl, but also alkoxyalkyl such as methoxymethyl, ethoxymethyl, propoxymethyl, butoxymethyl, methoxyethyl, ethoxyethyl, propoxyethyl, isopropoxyethyl, butoxyethyl, isobutoxyethyl, hydroxyalkoxyalkyl such as hydroxymethoxymethyl, 2-hydroxyethoxymethyl, 3-hydroxypropoxymethyl, 4-hydroxybuthoxymethyl, hydroxymethoxyethyl, hydroxymethoxypropyl hydroxymethoxybutyl, hydroxymethoxypentyl, hydroxymethoxyhexyl, polyhydroxyalkyl, hydroxypolyalkyleneoxyalkyl and similar groups.

The iodinated fatty acids having 4 to 24 carbon atoms and/or esters and/or mixtures thereof according to the invention may exist as isomeric mixtures or single isomers. If not specified both isomeric forms are intended. Where a compound of the invention contains one chiral centre, the iodiodinated compound can be provided as a single isomer (R or S) or as a mixture of isomers, for example a racemic mixture. Where an iodiodinated compound of the invention contains more than one chiral centre, the iodiodinated compound can be provided as an enantiomerically pure diastereoisomer or as a mixture of diastereoisomers.

In one embodiment, the iodiodinated fatty acids having 4 to 24 carbon atoms and/or esters and/or mixtures thereof according to the present invention has at least one asymmetric center. As a consequence of this asymmetric center, the iodinated compound of the present invention can occur in any of the possible stereoisomeric forms, and can be used in mixtures of stereoisomers, which can be optically active or racemic, or can be used alone as essentially pure stereoisomers, i.e., at least 95% pure. All asymmetric forms, individual stereoisomers and combinations thereof, are within the scope of the present invention.

According to an embodiment of the invention, the peroral contrast agent consisting in a biocompatible nano-emulsion of iodinated fatty acids having 4 to 24 carbon atoms and/or esters thereof can be used in a mixture comprising several or at least two iodinated fatty acids having different carbon chains of 4 to 24 carbon atoms.

In a preferred embodiment of the invention, the contrast agent consists in a biocompatible nano-emulsion of iodinated fatty acids having preferably 10 to 20 carbon atoms and more preferably 16 to 18 carbon atoms according to general formula I.

In an even preferred embodiment, the iodinated fatty acid is an iodinated linolenic acid. Preferably the iodiodinated fatty acids are periodinated.

In particular, the nano-emulsion preferably comprises biocompatible emulsifiers selected among lecithin, polyethylene glycol ethers with fatty alcohols, polysorbates and sorbitan esters or their mixtures. Lecithins, polysorbates (Tweens) and sorbitan esters (Spans) surfactants are preferred since they have a long and documented safe use in cosmetics, food products, and pharmaceutical formulations (oral, parenteral, and topical).

Preferably, the amount of the biocompatible emulsifiers in the nano-emulsion is between 5-30% (w/w) of the total nano-emulsion.

In one embodiment, the peroral CT contrast agent of the method according to the invention is adapted for non-invasive in vivo imaging, quantification, and/or monitoring of the activity of the brown and/or beige adipose tissue (BAT) in a subject.

According to another embodiment, the peroral CT contrast agent of the method according to the invention is adapted for non-invasive in vivo visualization and/or quantification of liver steatosis or liver tumors in a subject.

According to a further embodiment, the peroral CT contrast agent of the method according to the invention is adapted for non-invasive in vivo visualization of the heart and evaluation of the heart function.

According to a preferred embodiment, the peroral CT contrast agent of the method according to the invention is administrated at a dose corresponding to between 0.5 and 1.6 mg of iodine per gram of body weight.

It is another object of the present invention to provide a method of in vivo imaging with Computed Tomography brown and/or beige adipose tissue (BAT) in a subject, comprising administering orally a contrast agent comprising a biocompatible nano-emulsion of iodinated fatty acids having 4 to 24 carbon atoms and/or esters and/or salts and/or mixtures thereof according to general formula I (as defined above):

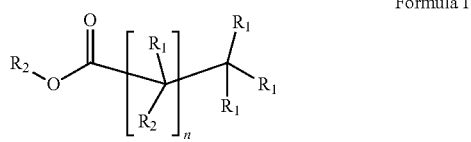

Formula I wherein n=2-22;
R$_1$ is H or I, with the provisions that the number of iodine atoms is 1 to 6, and that the iodine atoms are neither geminal nor vicinal;
and where R$_2$ is H, unsaturated or saturated, linear or branched alkyls, alkyls, alkoxyalkyl, hydroxyalkoxyalkyl, polyhydroxyalkyl, hydroxy poly alkyleneoxyalkyl.

In particular, the contrast agent of the invention consists in a biocompatible nano-emulsion of iodinated fatty acids having preferably 10 to 20 carbon atoms and more preferably 16 to 18 carbon atoms according to general formula I. In an even preferred embodiment, the iodinated fatty acid is an iodinated linolenic acid.

As defined above, the nano-emulsion preferably comprises biocompatible emulsifiers selected among lecithin, polyethylene glycol ethers with fatty alcohols, polysorbates and sorbitan esters or their mixtures.

Preferably, the amount of said biocompatible emulsifiers in the nano-emulsion is between 5-30% (w/w) of the total nano-emulsion.

In an embodiment, the contrast agent for the method of in vivo imaging with CT of the invention is adapted for non-invasive in vivo imaging, quantification, and/or monitoring of the activity of the brown and/or beige adipose tissue (BAT) in a subject.

According to a preferred embodiment, the peroral CT contrast agent of the method according to the invention is administrated at a dose corresponding to between 0.5 and 1.6 mg of iodine per gram of body weight.

It is a further object of the present invention to provide a method of in vivo imaging with Computed Tomography the heart or the liver in a subject, comprising administering orally a contrast agent comprising a biocompatible nano-emulsion of iodinated fatty acids having 4 to 24 carbon atoms and/or esters and/or salts and/or mixtures thereof according to general formula I (as defined above):

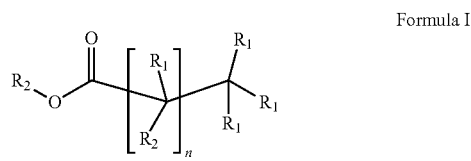

Formula I wherein n=2-22;
R$_1$ is H or I, with the provisions that the number of iodine atoms is 1 to 6, and that the iodine atoms are neither geminal nor vicinal;
and where R$_2$ is H, unsaturated or saturated, linear or branched alkyls, alkyls, alkoxyalkyl, hydroxyalkoxyalkyl, polyhydroxyalkyl, hydroxy poly alkyleneoxyalkyl.

In particular, the contrast agent of the method according to the invention consists in a biocompatible nano-emulsion of iodinated fatty acids having preferably 10-20 carbon atoms, and more preferably 16 to 18 carbon atoms according to general formula I. In an even preferred embodiment, the iodinated fatty acid is an iodinated linolenic acid.

As defined above, the nano-emulsion preferably comprises biocompatible emulsifiers selected among lecithin, polyethylene glycol ethers with fatty alcohols, polysorbates and sorbitan esters or their mixtures.

According to one embodiment, the peroral CT contrast agent of the method according to the invention is adapted for the visualization and/or quantification of liver steatosis or liver tumors in a subject.

The liver regulates metabolite flow in the body. Hepatocytes, which are the main cell type in the liver remove many materials from circulation, especially lipids. This property is of key importance to the development of liver steatosis, which is an accumulation of lipids into hepatocytes. An important source of lipid for the hepatocyte is circulating free fatty acids (FFAs) coming from lipolysis of stored triglycerides and dietary fat. Since the contrast agent of the invention is taken orally, it is assimilated as dietary fat. Thus advantageously, the nano emulsion of iodinated fatty acids (i.e. the contrast agent of the invention) is taken up by hepatocytes and this uptake will be increased in the case of steatosis.

According to another embodiment, the peroral CT contrast agent of the method according to the invention is adapted for the visualization of the heart and evaluation of its function in a subject.

Long chain fatty acids provide 70-80% of the energy for cardiac contractile activity. Fatty acids can enter the cardiomyocytes via simple diffusion, or via a protein-mediated mechanism. The contrast agent of the invention will therefore be taken up by heart muscle leading to visible enhancement of the cardiac muscle at the CT-scan.

Preferably, the peroral CT contrast agent of the method according to the invention is administrated at a dose corresponding to between 0.5 and 1.6 g of iodine per kg of body weight.

However in certain embodiments, the nano-emulsion may comprise, for example, at least about 0.01 mg of iodine per g of body weight of the peroral CT contrast agent of the invention. In other embodiments, the nano-emulsion may comprise between about 0.1% to about 75% of the weight of the unit, or between about 2% to about 20%, for example, and any range derivable therein.

In other non-limiting examples, a dose may also comprise from about 1 µg/kg/body weight, about 100 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 300 mg/kg/body weight, about 350 mg/kg/body weight, about 400 mg/kg/body weight, about 450 mg/kg/body weight, about 500 mg/kg/body weight, about 600 mg/kg/body weight, about 700 mg/kg/body weight, about 800 mg/kg/body weight, about 900 mg/kg/body weight, about 1000 mg/kg/body weight, about 2000 mg/kg/body weight to about 5000 mg/kg/body weight or more per administration, and any range derivable therein. In non-limiting examples of a derivable range from the numbers listed herein, a range of about 350 mg/kg/body weight to about 1000 mg/kg/body weight, about 50 µg/kg/body weight to about 500 mg/kg/body weight, and the like, can be administered.

In any case, the dose of the nano-emulsion that is to be used depends on the particular condition being diagnosed, the severity of the condition, the individual patient parameters including age, physical condition, size and weight, the duration of the imaging, the nature of concurrent therapy (if any) and other similar factors that are within the knowledge and expertise of the health practitioner. These factors are known to those of skill in the art and can be addressed with minimal routine experimentation. Accordingly, the optimum dosage may be determined by the practitioner who is diagnosing any particular patient.

Indeed, the main substrate of brown or beige adipocytes is thought to be fatty acids more than glucose[1]. It might also be the reason why the CT contrast agent is more taken up by brown adipocytes when mice are placed in cold environment or pharmaceutically treated in order to activate brown adipose tissue, meaning that one can obtain anatomical and functional information from the same CT scan. Other imaging methods for BAT such as [18]FDG-PET require activation of BAT, but the applicants observed that BAT and even beige adipose tissues could be imaged with the use of the novel CT contrast agent without prior activation of these tissues.

Secondly, the resolution of micro-CT is far better (between 10 and 100 micrometers) than the resolution of micro-PET (in the order of 1 millimeter) allowing the precise delineation of beige depots within white adipose tissue. That last property is of particular importance because no imaging method until now was able to highlight the beige adipose tissue within the white adipose tissue with such an accuracy. Indeed, beige adipocytes will take up the contrast agent which will result in considerably enhancing the contrast between beige and white adipocytes. On the other hand, the contrast agent is not detected in white adipocytes.

To Applicants' knowledge, it is the first time that one can achieve this performance non-invasively and in-vivo. It allows to precisely delineate small beige depots around the heart and vessels which is almost impossible with [18]FDG-PET due to the spillover effect from the heart signal itself. The possibility to non-invasively and precisely study the browning of PVAT (perivascular adipose tissue) and cardiac adipose tissue could also help in the evaluation of their role in cardiovascular disease such as atherosclerosis or hypertension. Applicants were also able to clearly identify in the mouse new beige depots which were poorly described until now, such as in the groin area or behind the knee in the popliteal area. Furthermore, Applicants were able to show a regionalization of the beige depot in different lobules within the inguinal fat pad.

Applicants also introduce the CT scan as a tool to monitor an indication of metabolic activity of a tissue, usually reserved to PET scan. Indeed, Applicants showed that conditions which activate brown or beige fat, such as low temperature or adrenergic activation via beta-3 receptors leads to an increase in the uptake of the CT contrast agent. More strikingly, Applicants also showed that the CT contrast agent of the invention, composed of fatty acids is detectable even in the condition of low brown adipose tissue activation which is really challenging with the use of PET given the acceptable limits of radiation exposure of volunteers. Fatty acids tracer for PET, such as $^{18}$F-fluoro-thiaheptadecanoic acid (18FTHA)[4] was already tested for BAT imaging but seems to offer low signal in human.

Preparation:

It is understood that any suitable method for preparing the iodinated fatty acids having 4 to 24 carbon atoms and/or esters thereof of formula (I) known to the skilled in the art may be encompassed by the scope of the present invention.

Chemical Synthesis

Linear or branched unsaturated fatty acids or its derivatives of natural, semisynthetic or synthetic origin can be used as starting materials to yield iodinated molecules of interest. The number of double bonds can vary from 1-6.

Synthesis of Monoiodostearic Acid

Phosphorous pentoxide (170 mg, 1.0 mmol) was added slowly to orthophosphoric acid (1.0 mL) under magnetic stirring. Oleic acid (141 mg, 0.5 mmol) and sodium iodide (150 mg, 1.0 mmol) were added and the reaction mixture heated at 70° C. under reflux cooling. After 24 h the reaction mixture was cooled to ambient temperature and the acid separated from the crude product. Dichloromethane (20 mL) was added and the organic phase washed with sodium thiosulfate (0.1 M) until the organic phase becomes colourless. The organic phase was washed with brine and dried over sodium sulphate. The solvent was evaporated under reduced pressure giving colourless oil which was purified by Flash chromatography using dichloromethane/methanol gradient (181 mg, 0.44 mmol, 88% yield).

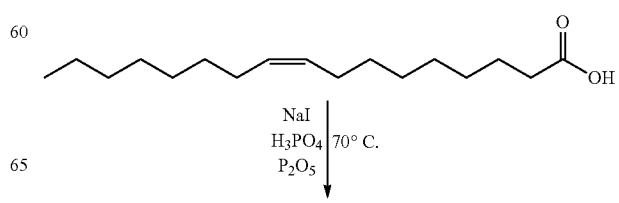

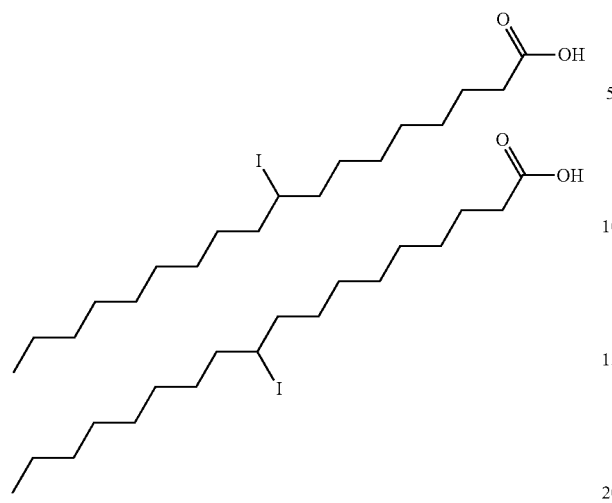

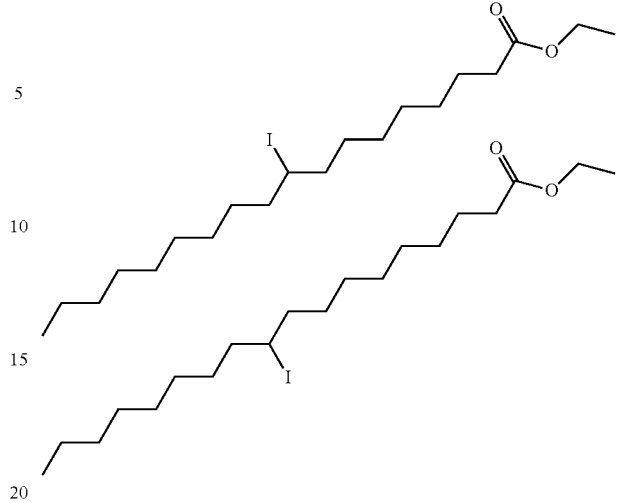

Synthesis of Ethyl Monoiodostearic Acid

Ethyl oleate was synthesized according to published procedures. Briefly, oleic acid (282 mg, 1 mmol), ethyl alcohol (170 mmol, 15 mL) and SnCl$_2$ (19 mg, 0.1 mmol were stirred at 60° C. After for 16 h the reaction mixture was cooled to ambient temperature and the solvent evaporated under reduced pressure. Dichloromethane (50 mL) was added and the organic phase washed with water, saturated solution of NaHCO$_3$ and brine. The organic phase was dried with Na$_2$SO$_4$ and the solvent evaporated under reduced pressure yielding colourless oil (282 mg, 95% yield).

Phosphorous pentoxide (170 mg, 1.0 mmol) was added slowly to orthophosphoric acid (1.0 mL) under magnetic stirring. Ethyl oleate (148 mg, 0.5 mmol) and sodium iodide (150 mg, 1.0 mmol) were added and the reaction mixture heated at 70° C. under reflux cooling. After 24 h the reaction mixture was cooled to ambient temperature and the acid separated from the crude product. Dichloromethane (20 mL) was added and the organic phase washed with sodium thiosulfate (0.1 M) until the organic phase becomes colourless. The organic phase was washed with brine and dried over sodium sulphate. The solvent was evaporated under reduced pressure giving colourless oil which was purified by Flash chromatography using dichloromethane/methanol gradient (170 mg, 0.39 mmol, 78% yield).

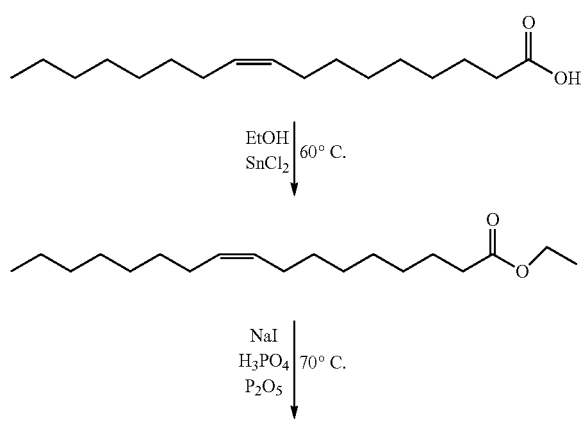

The described syntheses give structures with the following sub-formulae A, B, and C depending on the starting material used.

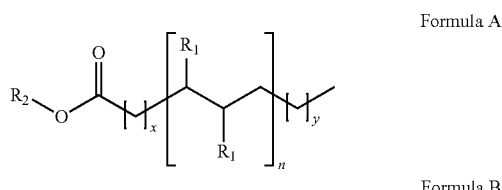

Formula A

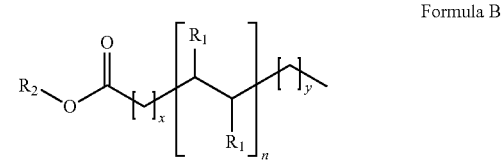

Formula B

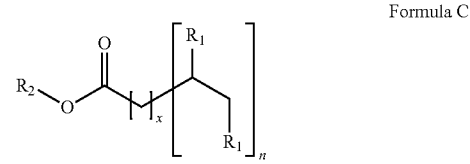

Formula C where n is an integer=1-6, and x=0-20 and y=0-20 and x+y≤20 with the provision that the total number of carbon atoms in Formulae A, B or C respectively is 24; and where R$_2$ group may be mono or poly-substituted.

Preferably, R$_2$ groups can include but are not limited to set of alkyl substituents such as methyl, ethyl, propyl, isopropyl, butyl, isobutyl, t-butyl, cyclopropylmethyl, pentyl, isopentyl, hexyl, isohexyl, heptly, isoheptyl, octyl, isooctyl, 2-propenyl, allyl, crotyl, 1-butenyl, 2-butenyl, butadienyl, ethynyl, 1-propynyl, 2-propynyl, 1-butynyl, 2-butynyl, 3-butynyl and propagyl, cyclopentyl, cyclohexyl, cycloheptyl, admantyl; aryls substituents such as phenyl, naphthyl, anisyl, toluyl, xylenyl, aryloxy, aralkyl, aralkyloxy, heteroaryl groups(pyrimidine, morpholine, piperazine, piperidine, thiophene), 1-cyclohexylpropyl, or haloalkyls substituents such as fluoromethyl, 1-fluoroethyl, 2-fluoroethyl, difluoromethyl, trifluoromethyl and pentafluoroethyl, chlorodimethyl, chloromethyl, 2-chloroethyl, 2,4-dichlorophenyl, 1,1,2,2-tetrachloroethyl, 1-chlorobutyl, and 4-chlorobenzyl.

It can also include substituted alkyl groups such as 9-fluorenylmethyl, methoxyethoxymethyl, tetrahydropyranyl, pivalyloxymethyl, phenylacetoxymethyl, phenacyl and substituted phenacyl such as p-bromophenacyl, p-methoxyphenacyl, and also t-butyl, 3-methyl-3-pentyl, cyclopentyl, cycohexyl, allyl, 3-buten-1-yl, cinnamyl, oxazole, and 2-alkyl-1,3-oxazoline.

It can also include alkylaryl such as benzyl, substituted benzyl such as triphenylmethyl, p-methoxybenzyl, 4-picolyl, dipohenylmethyl phenylethyl, substituted phenylethyl, but also alkoxyalkyl such as methoxymethyl, ethoxymethyl, propoxymethyl, butoxymethyl, methoxyethyl, ethoxyethyl, propoxyethyl, isopropoxyethyl, butoxyethyl, isobutoxyethyl, hydroxyalkoxyalkyl such as hydroxymethoxymethyl, 2-hydroxyethoxymethyl, 3-hydroxypropoxymethyl, 4-hydroxybuthoxymethyl, hydroxymethoxyethyl, hydroxymethoxypropyl hydroxymethoxybutyl, hydroxymethoxypentyl, hydroxymethoxyhexyl, polyhydroxyalkyl, and hydroxypolyalkyleneoxyalkyl.

Nano-Emulsion:

Formulation optimization was done by experimental design. Several parameters have been assessed, including active CT ingredient, excipient(s) type and quantity, their compatibility, and method of preparation. The optimal formulation choice was based on physico-chemical properties, stability and biocompatibility.

Oil-in-water nano-emulsions were prepared in order to dissolve the iodinated fatty acids in water, which will improve their intestinal absorption. The emulsion formulation was improved in order to reach the fastest and the more complete absorption of the contrast agent. The aim of this last step is to reach the highest enhancement with the lower possible dose. Then, the contrast agent was tested in different conditions of brown fat activation in order to show its potential in the evaluation of the brown fat metabolism.

The following characteristics are to be achieved:

O/W nano-emulsion
Minimal amount of emulsifiers
Low viscosity
Biocompatibility (non-toxic and non-irritating at required doses)
Prolonged stability of nano-emulsions upon storage at 4° C.
Materials and process cost effectiveness The proposed short-list of excipients and their mixtures have been tested:

Polysorbates (Tween) 20, 40, 60, 80
Sorbitan esters (Span) 20, 40, 60, 80, 85
Polyoxyethylene fatty alcohol ethers (Brij) 30, 35, 52, 58, 72, 78, 92, 98)
Lecithins
Alkyl polyglycosides
Cetomacrogol 1000
Cetostearyl alcohol
Cetyl alcohol
Cocamide MEA
Cocamide DEA
Decyl glucoside
Decyl polyglucose
Glycerol monostearate
Isoceteth-20
Lauryl glucoside
Maltosides
Monolaurin
Mycosubtilin
Nonidet P-40
Nonoxynol-9
Nonoxynols
NP-40
Octaethylene glycol monododecyl ether
N-Octyl beta-D-thioglucopyranoside
Octyl glucoside
Oleyl alcohol
PEG-10 sunflower glycerides
Pentaethylene glycol monododecyl ether
Polidocanol
Poloxamer
Poloxamer 407
Polyethoxylated tallow amine
Polyglycerol polyricinoleate
Sorbitan tristearate
Stearyl alcohol
Surfactin
Triton X-100

Lecithins, polysorbates (Tweens) and sorbitan esters (Spans) surfactants are preferred since they have a long and documented safe use in cosmetics, food products, and pharmaceutical formulations (oral, parenteral, and topical).

The fatty acid or its derivative (dissolved in an organic solvent or neat) can be added to ion-free water, preferably containing an emulsifier, with vigorous agitation at a temperature above the melting point of the fatty acid, to produce a finely dispersed oil-in-water emulsion. Agitation may be effected by any known means, e.g. by the use of a high shear agitator or ultrasonically.

The amount of iodinated fatty acid or its derivatives should be at least 10% and preferably at least 20% by weight of the concentrated emulsion; a content of 30% is generally preferred; but emulsions as concentrated as 40% can be prepared in some cases a small amount of an emulsifying agent is preferably included in the composition.

When an emulsifier is used the viscosity of the emulsion will vary with the water/oil phase ratio and usually passes through a maximum value as the water/fatty acid ratio is increased. In order to obtain a fine emulsion it is preferable to agitate for a time with the Water/fatty acid ratio near to or slightly in excess of that required for maximum viscosity and then add further ion-free water with continued agitation to give the desired iodinated fatty acid concentration. The emulsion is then allowed to cool to room temperature.

It is also an object of the present invention to provide a method of in vitro imaging of the brown and beige adipose tissue of a subject's sample such as an organ or cell cultures using a Computed Tomography contrast agent consisting of a biocompatible nano-emulsion of iodinated fatty acids having 4 to 24 carbon atoms and/or esters and/or salts and/or mixtures thereof according to general formula I:

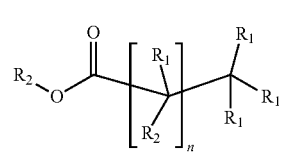

Formula I wherein n=2-22;

$R_1$ is H or I, with the provisions that the number of iodine atoms is 1 to 6, and that the iodine atoms are neither geminal nor vicinal;

and where $R_2$ is H, unsaturated or saturated, linear or branched alkyls, alkoxyalkyl, hydroxyalkoxyalkyl, polyhydroxyalkyl, hydroxy poly alkyleneoxyalkyl.

It is another object of the present invention to provide a composition comprising a biocompatible nano-emulsion of iodinated fatty acids having 4 to 24 carbon atoms and/or esters and/or salts and/or mixtures thereof according to general formula I (as defined above):

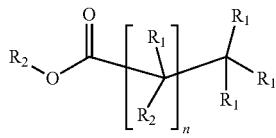

Formula I wherein n=2-22;

$R_1$ is H or I, with the provisions that the number of iodine atoms is 1 to 6, and that the iodine atoms are neither geminal nor vicinal;

and where $R_2$ is H, unsaturated or saturated, linear or branched alkyls, alkyls, alkoxyalkyl, hydroxyalkoxyalkyl, polyhydroxyalkyl, hydroxy poly alkyleneoxyalkyl;

for use as a non-invasive peroral Computed Tomography contrast agent for in vivo imaging the brown and/or beige adipose tissue in a subject.

In particular, the contrast agent of the invention consists in a biocompatible nano-emulsion of iodinated fatty acids having preferably 10-20 carbon atoms and more preferably 16 to 18 carbon atoms according to general formula I. In an even preferred embodiment, the iodinated fatty acid is an iodinated linolenic acid.

As defined above, the nano-emulsion preferably comprises biocompatible emulsifiers selected among lecithin, polyethylene glycol ethers with fatty alcohols, polysorbates and sorbitan esters or their mixtures.

It is yet a further object of the present invention to provide a composition comprising a biocompatible nano-emulsion of iodinated fatty acids having 4 to 24 carbon atoms and/or esters and/or salts and/or mixtures thereof according to general formula I (as defined above):

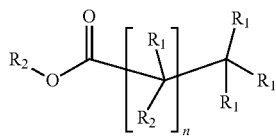

Formula I wherein n=2-22;

$R_1$ is H or I, with the provisions that the number of iodine atoms is 1 to 6, and that the iodine atoms are neither geminal nor vicinal;

and where $R_2$ is H, unsaturated or saturated, linear or branched alkyls, alkyls, alkoxyalkyl, hydroxyalkoxyalkyl, polyhydroxyalkyl, hydroxy poly alkyleneoxyalkyl;

for use as a non-invasive peroral Computed Tomography contrast agent for in vivo imaging of the heart or the liver in a subject.

In particular, the contrast agent of the invention consists in a biocompatible nano-emulsion of iodinated fatty acids having preferably 10 to 20 carbon atoms and more preferably 16 to 18 carbon atoms according to general formula I. In an even preferred embodiment, the iodinated fatty acid is an iodinated linolenic acid.

As defined above, the nano-emulsion preferably comprises biocompatible emulsifiers selected among lecithin, polyethylene glycol ethers with fatty alcohols, polysorbates and sorbitan esters or their mixtures.

According to one embodiment of the invention, the peroral CT contrast agent of the invention is adapted for the visualization and/or quantification of liver steatosis or liver tumors in a subject.

Kits comprising the Computed Tomography contrast agent of the invention are also envisioned.

Another object of the present invention is to provide a method for preventing and/or treating a patient suspected of suffering or suffering from a heart or liver disease, said method comprising the steps of:

a) administrating to said patient the peroral Computed Tomography contrast agent of the invention consisting of a biocompatible nano-emulsion of iodinated fatty acids having 4 to 24 carbon atoms and/or esters and/or salts and/or mixtures thereof according to general formula I:

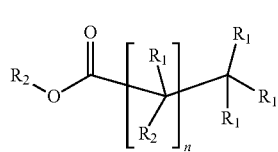

Formula I where n=2-22;

$R_1$ is H or I, with the provisions that the number of iodine atoms is 1 to 6, and that the iodine atoms are neither geminal nor vicinal;

and where $R_2$ is H, unsaturated or saturated, linear or branched alkyls, alkoxyalkyl, hydroxyalkoxyalkyl, polyhydroxyalkyl, hydroxy poly alkyleneoxyalkyl.

b) and subsequently administering to said patient the adapted therapy depending on the results of the in vitro imaging of step a) of the heart and/or liver of said patient.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

In vivo CT scan was performed before and at several time points after the application of the contrast agents in the mouse. The mouse is anesthetized with isoflurane and placed in the CT scan available at the small animal imaging facility. The scan last approximately 10 minutes per mouse. The mouse is then put in its cage and will recover from anaesthesia within few minutes. Images are then transferred to another computer for analysis of the brown fat enhancement.

In vivo activation or inhibition of the brown adipose tissue is done by modulating the housing temperature of the mice. Mice is housed for 1 week in a specific thermostatic chamber in order to activate brown adipose tissue thermogenesis (at 6° C.). After 1 week, the contrast agent is given orally to the mice and the mice are scanned in the CT scanner to evaluate the brown fat enhancement in these different conditions of activation.

Example 1: Synthesis of 9(10)-Iodooctadecanoic Acid

Phosphorous pentoxide (170 mg, 1.0 mmol) was added slowly to orthophosphoric acid (1.0 mL) under magnetic stirring. Oleic acid (141 mg, 0.5 mmol) and sodium iodide were added and the reaction mixture heated at 70° C. under reflux cooling. After 24 h the reaction mixture was cooled to ambient temperature and the acid separated from the crude product. Dichloromethane (20 mL) was added and the organic phase washed with sodium thiosulfate (0.1 M) until the organic phase becomes colourless. The organic phase was washed with brine and dried over sodium sulphate. The solvent was evaporated under reduced pressure giving colourless oil which was purified by Flash chromatography using dichloromethane/methanol gradient (181 mg, 0.44 mmol, 88% yield). $^1$H NMR (600 MHz, CDCl$_3$) δ 4.07-4.02 (m, 1H), 2.28 (t, J=7.5 Hz, 2H), 1.78 (m, 2H), 1.60 (m, 4H), 1.45 (m, 2H), 1.36-1.16 (m, 22H), 0.81 (t, J=7.0 Hz, 3H). LRMS (ESI): m/z calculated for [M+K]$^+$ 449.1, found 448.1.

Example 2: Synthesis of 9(10), 12(13)-Diiodooctadecanoic Acid

Phosphorous pentoxide (340 mg, 2.0 mmol) was added slowly to orthophosphoric acid (2.0 mL) under magnetic stirring. Linoleic acid (280 mg, 1.0 mmol) and sodium iodide (500 mg, 3.33 mmol) were added and the reaction mixture heated at 70° C. under reflux cooling. After 24 h the reaction mixture was cooled to ambient temperature and the acid separated from the crude product. Dichloromethane (20 mL) was added and the organic phase washed with sodium thiosulfate (0.1 M) until the organic phase becomes colourless. The organic phase was washed with brine and dried over sodium sulphate. The solvent was evaporated under reduced pressure giving colourless oil which was purified by Flash chromatography using dichloromethane/methanol gradient (407 mg, 0.76 mmol, 76% yield). $^1$H NMR (600 MHz, CDCl$_3$) δ 4.15-4.07 (m, 2H), 2.41-2.34 (m, 2H), 2.11-2.02 (m, 2H), 1.96-1.82 (m, 2H), 1.76-1.62 (m, 4H), 1.58-1.50 (m, 2H), 1.46-1.23 (m, 16H), 0.95-0.88 (m, 3H). LRMS (ESI): m/z calculated for [M+Na]$^+$ 559.0, found 558.9.

Example 3: Preparation of Nano-Emulsion

The nano-emulsion was prepared by mixing the 200 mg iodinated linoleic acid, 100 mg of excipients (e.g. Tween 80/Span 80, 90/10 ratio) and 200 mg of MilliQ water. The mixture was cooled using an ice bath whilst being homogenized by ultrasonication. The ultrasonicator was set at 30% amplitude for 2 min using a 5 s pulse followed by 5 s pause sequence giving a homogenous nano-emulsion.

Example 4: Synthesis and Characterization of a CT Contrast Agent Used to Image and Quantify BAT Metabolic Activity To investigate in vivo the brown and beige adipocytes, the nano-emulsion was given orally to a mouse housed at 6° c. during 1 week to activate brown fat activity. A CT scan was performed before and after the oral ingestion of the CT contrast agent of the invention (FIG. 3), containing ethyl 9 (10), 12 (13)dioiodooctadecanoate. As shown in the FIG. 4, the uptake kinetics by brown adipose tissue reached a plateau at approximately 24 hours post-ingestion in activated BAT. Furthermore, as shown in FIG. 5, the CT contrast agent allowed to build a map of all the different brown and beige adipose depots in the whole body of the mouse studied in vivo. Thanks to the high resolution of the CT, each depot was clearly identified, as illustrated on the FIG. 5. In addition, Applicants were not only able to identify all known brown or beige depots, but also some depots not seen in vivo until now, such as in the groin and the popliteal areas.

The results obtained by classical dissection of brown and white fat depots and those provided by Applicants' novel in vivo approach were compared, as depicted by FIG. 5, which is a representation of each of the individual brown or beige adipose tissue depot obtained with the CT contrast agent of the invention.

Example 5: Synthesis of Ethyl 16-Iodohexadecanoate

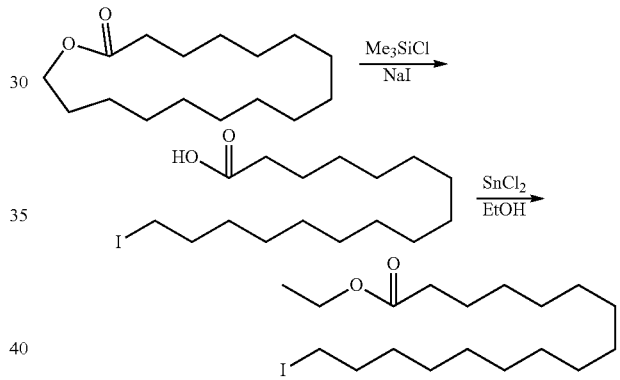

Example 6: Synthesis of 16-Iodohexadecanoic Acid 16-hexadecanolide (2.00 g, 7.86 mmol, 1 eq), sodium iodide (3.54 g, 23.6 mmol, 3 eq), chlorotrimethylsilane (2.99 mL (2.56 g), 23.6 mmol, 3 eq) and acetonitrile (25 mL, c=0.31 M) were stirred at reflux under nitrogen atmosphere overnight. Water (20 mL) and ether (50 mL) were added to the reaction mixture. The organic phase was washed with water, sodium thiosulfate, saturated brine and dried over sodium sulfate. The organic phase was filtered off and evaporated under reduced pressure to obtain a white solid (2.88 g, 7.53 mmol, 96% yield). 1H NMR (600 MHz, CDCl3) δ 3.19 (t, J=7.1 Hz, 2H), 2.35 (t, J=7.5 Hz, 2H), 1.82 (p, J=7.1 Hz, 2H), 1.63 (p, J=7.5 Hz, 2H), 1.43-1.19 (m, 23H). 13C NMR (151 MHz, CDCl3) δ 179.62, 34.09, 33.72, 30.66, 29.77, 29.75, 29.73, 29.69, 29.57, 29.39, 29.21, 28.70, 24.83, 7.71.

Example 7: Synthesis of Ethyl 16-Iodohexadecanoate 16-iodohexadecanoic acid (100 mg, 0.262 mmol, 1 eq), tin (II) chloride (19.8 mg, 0.105 mmol, 0.4 eq) and ethanol (5 mL, c=0.052 M) were stirred under nitrogen atmosphere overnight at reflux. The reaction mixture was evaporated under reduced pressure. The crude was purified by flash chromatography using cyclohexane/ether gradient to obtain a white solid (94.0 mg, 0.229 mmol, 88% yield). ESI MS 433.2 [M+Na]+. 1H NMR (600 MHz, CDCl3) δ 4.12 (m, J=7.1 Hz, 2H), 3.19 (t, J=7.1 Hz, 2H), 2.28 (t, J=7.6 Hz, 2H), 1.82 (p, J=7.1 Hz, 2H), 1.61 (p, J=7.4 Hz, 2H), 1.45-1.19 (m, 23H). 13C NMR (151 MHz, CDCl3) δ 174.10, 60.31, 34.56, 33.72, 30.66, 29.78, 29.75, 29.74, 29.69, 29.60, 29.57, 29.42, 29.30, 28.70, 25.15, 14.41, 7.66.

Example 8: Synthesis of Ethyl 12-Iodododecanoate

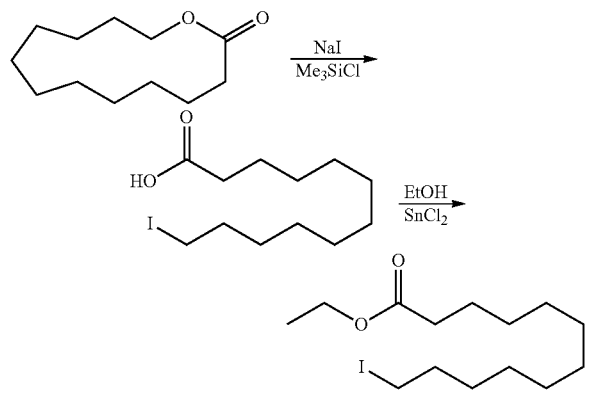

Example 9: Synthesis of 12-Iodohexadecanoic Acid

Oxacyclotridecan-2-one (1.00 g, 5.00 mmol, 1 eq) 16-hexadecanolide (2.00 g, 7.86 mmol, 1 eq), sodium iodide (2.25 g, 15.0 mmol, 3 eq) and chlorotrimethylsilane (1.90 mL (1.63 g), 15.0 mmol, 3 eq) and acetonitrile (25 mL, c=0.31 M) were stirred at reflux under nitrogen atmosphere overnight. Water (20 mL) and ether (50 mL) were added to the reaction mixture. The organic phase was washed with water, sodium thiosulfate, saturated brine and dried over sodium sulfate. The organic phase was filtered off and evaporated under reduced pressure to obtain a light yellowish solid (1.62 g, 4.97 mmol, 98% yield). ESI MS 325.2 [M−H]−. 1H NMR (600 MHz, CDCl3) δ 3.19 (t, J=7.0 Hz, 2H), 2.35 (t, J=7.5 Hz, 2H), 1.82 (p, J=7.1 Hz, 2H), 1.63 (p, J=7.5 Hz, 2H), 1.44-1.22 (m, 14H). 13C NMR (151 MHz, CDCl3) δ 179.47, 34.06, 33.70, 30.64, 29.59, 29.52, 29.50, 29.35, 29.18, 28.67, 24.82, 7.71.

Example 10: Synthesis Ethyl 12-Iodododecanoate 12-iodohexadecanoic acid (800 mg, 2.45 mmol, 1 eq), tin (II) chloride (200 mg, 1.05 mmol, 0.4 eq) and ethanol (50 mL, c=0.052 M) were stirred under nitrogen atmosphere overnight at reflux. The reaction mixture was evaporated under reduced pressure. The crude was purified by flash chromatography using cyclohexane/ether gradient to obtain a white solid (1.06 g, 2.58 mmol, 66% yield). ESI MS 355.1 [M+H]+. 1H NMR (600 MHz, CDCl3) δ 4.11 (q, J=7.1 Hz, 2H), 3.18 (t, J=7.1 Hz, 2H), 2.27 (t, J=7.6 Hz, 2H), 1.81 (p, J=7.1 Hz, 2H), 1.60 (p, J=7.4 Hz, 2H), 1.37 (q, J=6.8, 6.4 Hz, 2H), 1.33-1.20 (m, 15H). 13C NMR (151 MHz, CDCl3) δ 174.03, 60.28, 34.52, 33.69, 30.63, 29.58, 29.51, 29.37, 29.26, 29.25, 28.66, 25.11, 14.40, 7.51.

Example 11: Synthesis of 9(10),12(13)-Diodooctadecanoic Acid

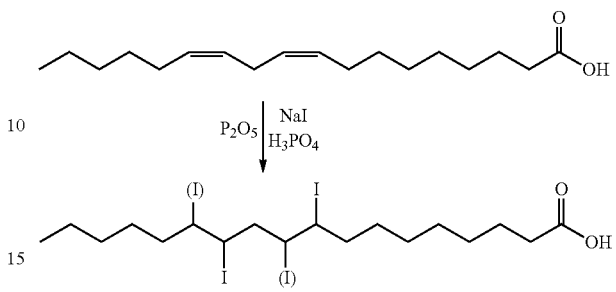

Phosphorus pentoxide (2.82 g, 20.0 mmol, 2 eq), linoleic acid (3.00 g, 10.7 mmol, 1 eq), sodium iodide (6.00 g, 40.0 mmol, 4 eq) and phosphoric acid (20 mL, c=0.50 M) were stirred under nitrogen atmosphere at 70° C. for 12 h and for 1 h30 at room temperature under low stirring. Ether (50 mL) and water (20 mL) were added to the reaction mixture. The aqueous phase was extracted with ethyl acetate and the combined organic phases were washed with sodium thiosulfate (0.1 M), saturated brine, dried over sodium sulfate, filtered off and evaporated under reduced pressure. The crude product was purified by flash chromatography using dichloromethane/methanol gradient+0.1% acetic acid to obtain a light yellowish solid (4.875 g, 9.09 mmol, 85% yield). ESI MS 558.5 [M+Na]+, 553.5 [M+NH4]+. 574.5 [M+K]+. 1H NMR (600 MHz, CDCl3) δ 4.14-4.05 (m, 2H), 2.35 (m, 2H), 1.96-1.80 (m, 2H), 1.76-1.61 (m, 3H), 1.57-1.49 (m, 3H), 1.46-1.27 (m, 16H), 0.90 (7, J=6.8 Hz, 3H).

Example 12: Synthesis of Triiodooctadecanoic Acid and Ethyl Triiodooctadecanoate

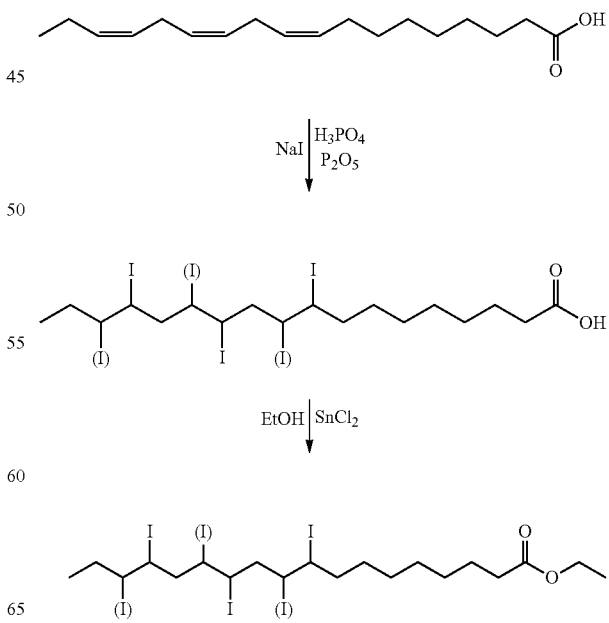

Example 13: Synthesis of Tetraiodoicosanoic Acid and Ethyl Tetraiodoicosanoate
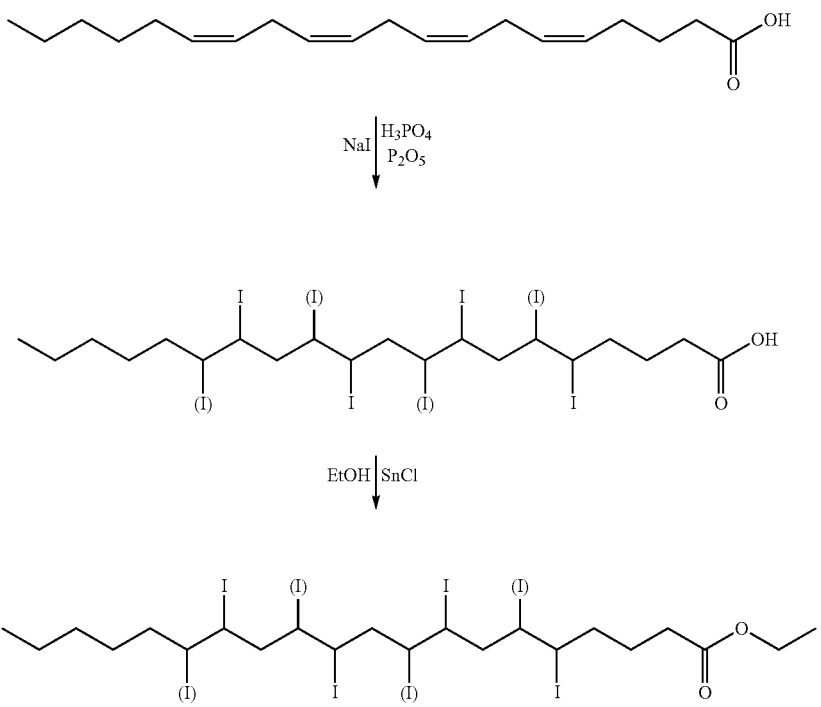
Example 14: Synthesis of Pentaiodoicosanoic Acid and Ethyl Pentaiodoicosanoate
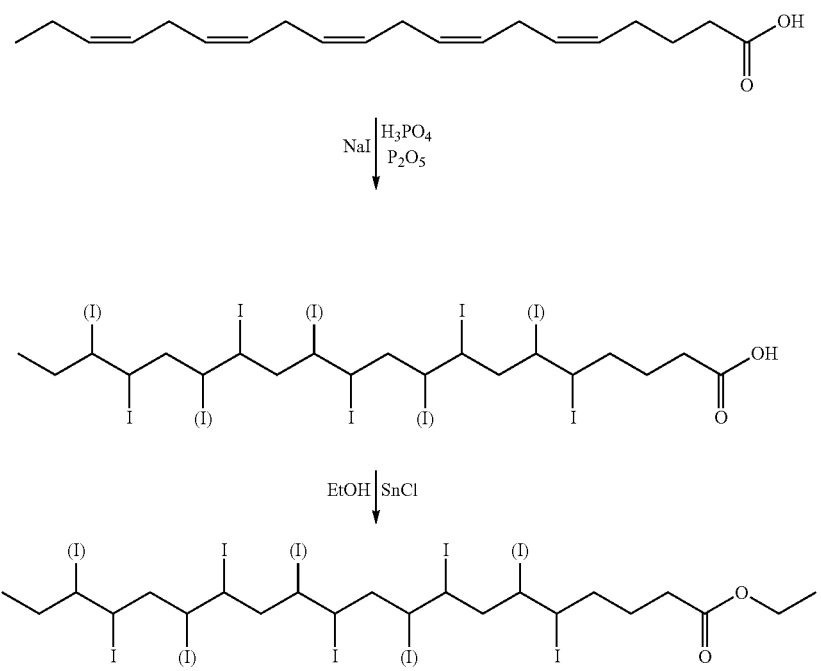

Example 15: Synthesis of Hexaiododocosanoic Acid and Ethyl Hexaiododocosanoate

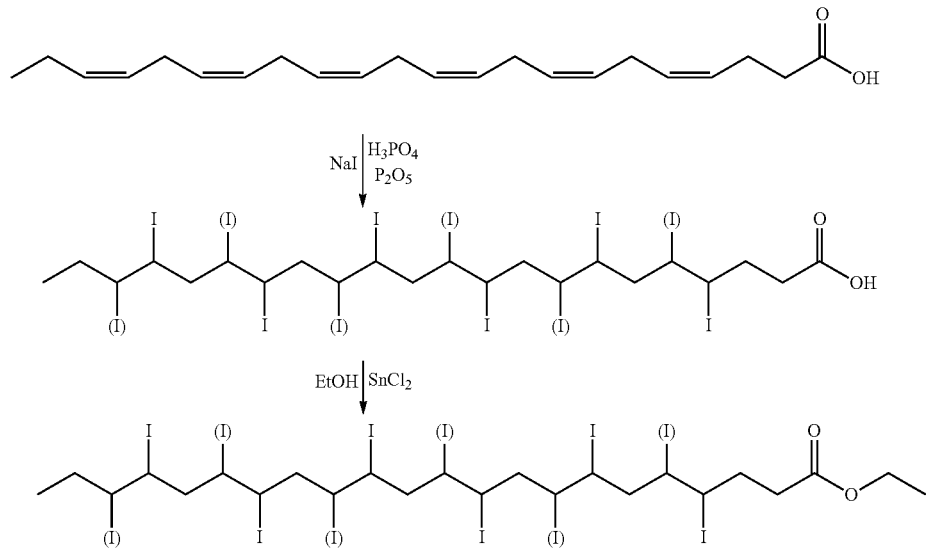

Example 16: Characterization of a CT Contrast Agent Used to Image Heart and Liver To investigate in vivo the heart and liver, the nano-emulsion of the invention was given orally to a mouse. A CT scan was performed before and 7 hours after the oral ingestion of the invention CT contrast agent, containing iodinated ethyl esters of linoleic (65%), oleic (30%) and linolenic (4%) acids (FIG. 6). As shown in FIG. 6a, the contrast agent is taken up by the heart cardiomyocytes, revealing the walls of the left ventricle. The heart walls enhancement allows for the measurement of anatomical parameters such as the thickness or the volume of the cardiac muscle. As shown in FIG. 6b, the contrast agent is also taken up by the liver, increasing its contrast.

REFERENCES

1. Bartell A, Bruns O T, Reimer R, et al. Brown adipose tissue activity controls triglyceride clearance. Nat Med. 2011; 17(2):200-205.
2. Cannon B, Houstek J, Nedergaard J. Brown adipose tissue. More than an effector of thermogenesis? Ann N Y Acad Sci. 1998; 856:171-187.
3. Guerra C, Koza R A, Yamashita H, Walsh K, Kozak L P. Emergence of brown adipocytes in white fat in mice is under genetic control. Effects on body weight and adiposity. J Clin Invest. 1998; 102(2):412-420.
4. Blondin D P, Labbe S M, Noll C, et al. Selective Impairment of Glucose but Not Fatty Acid or Oxidative Metabolism in Brown Adipose Tissue of Subjects With Type 2 Diabetes. Diabetes. 2015; 64(7):2388-2397.
5. Ferreira A B, Cardoso A L, da Silva M J. Novel and Highly Efficient SnBr2-Catalyzed Esterification Reactions of Fatty Acids: The Notable Anion Ligand Effect. Catal Lett. 2013; 143(11):1240-1246.

The invention claimed is:
1. A method of in vivo imaging with Computed Tomography brown and/or beige adipose tissue (BAT) in a subject, comprising a step of administering orally a contrast agent comprising iodinated fatty acids having 4 to 24 carbon atoms and/or esters and/or salts and/or mixtures thereof according to general formula I, and a step of performing a computed tomography imaging:

Formula I wherein n=2-22;
R$_1$ is H or I, with the provisions that the number of iodine atoms is 1 to 6, and that the iodine atoms are neither geminal nor vicinal;
and where R$_2$ is H, unsaturated or saturated, linear or branched alkyls, alkyls, alkoxyalkyl, hydroxyalkoxyalkyl, polyhydroxyalkyl, hydroxy poly alkyleneoxyalkyl.

2. The method of in vivo imaging with CT according to claim 1, wherein the iodinated fatty acids having 4 to 24 carbon atoms and/or esters and/or salts and/or mixtures thereof according to general formula I is in the form of a biocompatible nano-emulsion.

3. The method of in vivo imaging with CT according to claim 1, wherein the contrast agent is adapted for non-invasive in vivo imaging, quantification, and/or monitoring of the activity of the brown and/or beige adipose tissue (BAT) in said subject.

4. The method of in vivo imaging with CT according to claim 2, wherein the contrast agent consists in a biocompatible nano-emulsion of iodinated fatty acids having 10 to 20 carbon atoms according to general formula I.

5. The method of in vivo imaging with CT according to claim 2, wherein the contrast agent consists in a biocompatible nano-emulsion of iodinated fatty acids having 16 to 18 carbon atoms according to general formula I.

6. The method of in vivo imaging with CT according to claim 1, wherein the iodinated fatty acid is obtained by iodinating linolenic acid.

7. The method of in vivo imaging with CT according to claim 2, wherein the nano-emulsion comprises biocompatible emulsifiers selected among lecithin, polyethylene glycol ethers with fatty alcohols, polysorbates and sorbitan esters or their mixtures.

8. The method of in vivo imaging with CT according to claim 7, wherein the amount of said biocompatible emulsifiers in the nano-emulsion is between 5-30% (w/w) of the total nano-emulsion.

9. The method of in vivo imaging with CT according to claim 1, wherein the CT contrast agent is administered at a dose corresponding to between 0.5 and 1.6 mg of iodine per gram of body weight.

10. A method of in vivo imaging with Computed Tomography the heart muscle in a subject, comprising a step of administering orally a contrast agent comprising iodinated fatty acids having 4 to 24 carbon atoms and/or esters and/or salts and/or mixtures thereof according to general formula I, and a step of performing a computed tomography imaging:

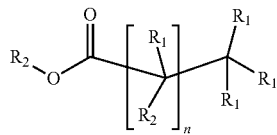

Formula I wherein n=2-22;

$R_1$ is H or I, with the provisions that the number of iodine atoms is 1 to 6, and that the iodine atoms are neither geminal nor vicinal;

and where $R_2$ is H, unsaturated or saturated, linear or branched alkyls, alkyls, alkoxyalkyl, hydroxyalkoxyalkyl, polyhydroxyalkyl, hydroxy poly alkyleneoxyalkyl.

11. The method of in vivo imaging with CT according to claim 10, wherein the iodinated fatty acids having 4 to 24 carbon atoms and/or esters and/or salts and/or mixtures thereof according to general formula I is in the form of a biocompatible nano-emulsion.

12. The method of in vivo imaging with CT according to claim 11, wherein the contrast agent consists in a biocompatible nano-emulsion of iodinated fatty acids having 16 to 18 carbon atoms according to general formula I.

13. The method of in vivo imaging with CT according to claim 10, wherein the iodinated fatty acid is obtained by iodinating linolenic acid.

14. The method of in vivo imaging with CT according to claim 10, wherein the contrast agent is for the visualization of the heart muscle and evaluation of its function in said subject.

15. The method of in vivo imaging with CT according to claim 10, wherein the CT contrast agent is administered at a dose corresponding to between 0.5 and 1.6 mg of iodine per gram of body weight.

* * * * *

UNITED STATES PATENT AND TRADEMARK OFFICE
CERTIFICATE OF CORRECTION

PATENT NO. : 11,654,202 B2
APPLICATION NO. : 16/637366
DATED : May 23, 2023
INVENTOR(S) : Laurent Vinet et al.

Page 1 of 4

It is certified that error appears in the above-identified patent and that said Letters Patent is hereby corrected as shown below:

In the Specification

Column 4, Line 10, delete:

" 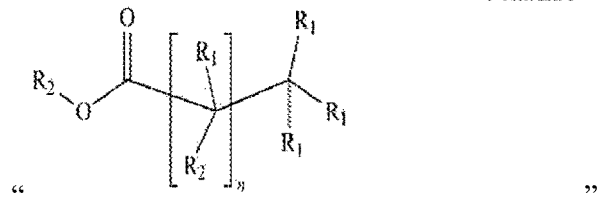 Formula I "

And insert:

-- Formula I 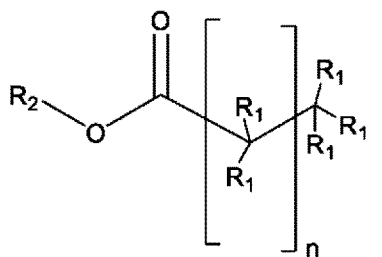 --

Column 8, Line 55, delete:

" 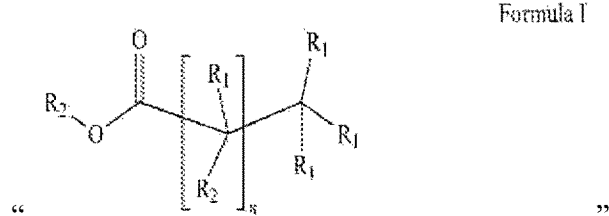 Formula I "

And insert:

Signed and Sealed this
Twenty-fifth Day of July, 2023

Katherine Kelly Vidal
*Director of the United States Patent and Trademark Office*

CERTIFICATE OF CORRECTION (continued)
U.S. Pat. No. 11,654,202 B2

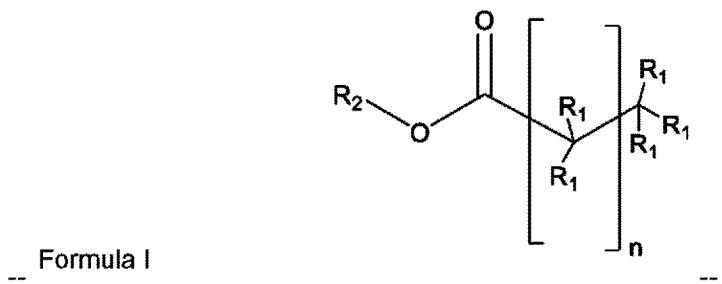

-- Formula I --

Column 11, Line 35, delete:

"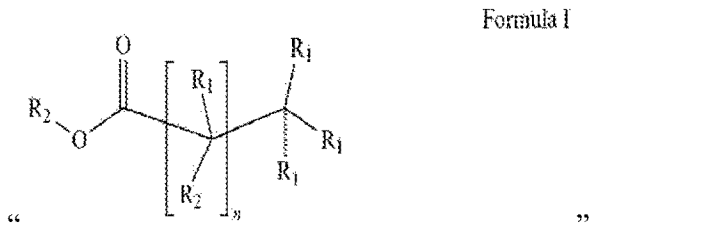 Formula I"

And insert:

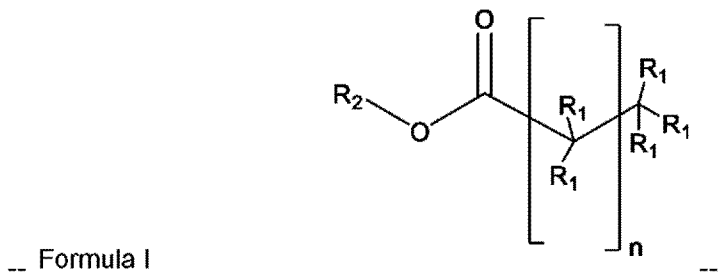

-- Formula I --

Column 12, Line 15, delete:

"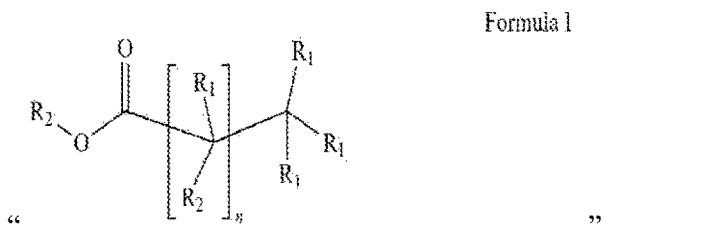 Formula I"

And insert:

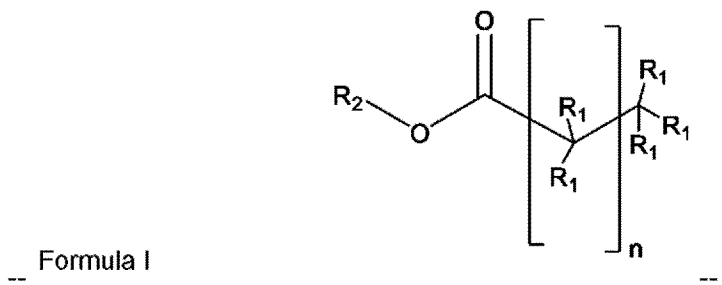

-- Formula I --

Column 18, Line 55, delete:

CERTIFICATE OF CORRECTION (continued)
U.S. Pat. No. 11,654,202 B2

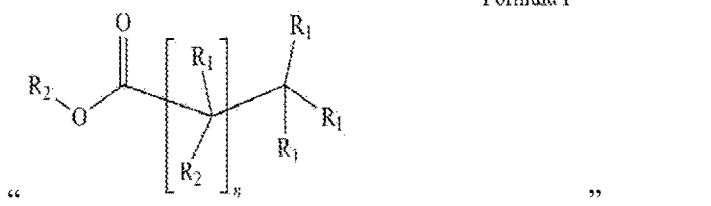

Formula I

And insert:

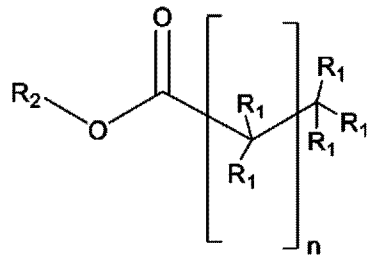

Formula I

Column 19, Line 5, delete:

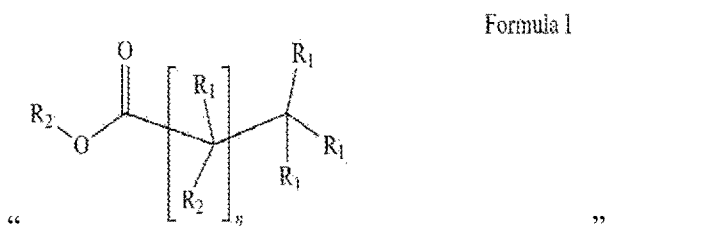

Formula I

And insert:

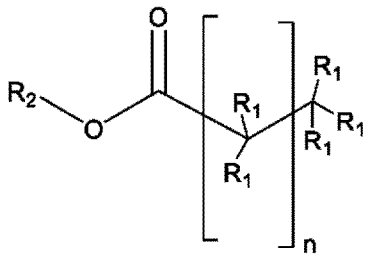

Formula I

Column 20, Line 20, delete:

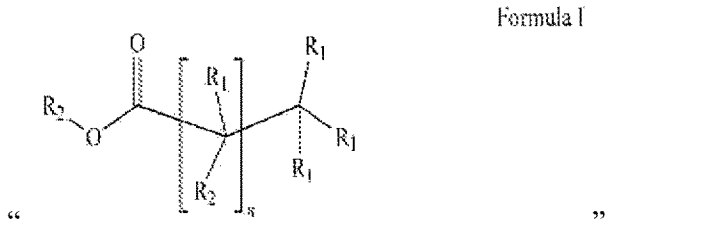

Formula I

And insert:

CERTIFICATE OF CORRECTION (continued)
U.S. Pat. No. 11,654,202 B2

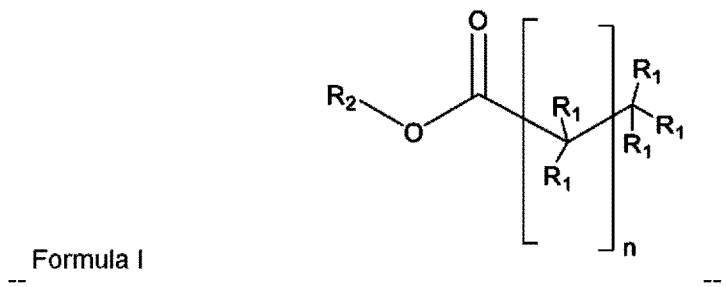

-- Formula I --

Column 28, Line 35, delete:

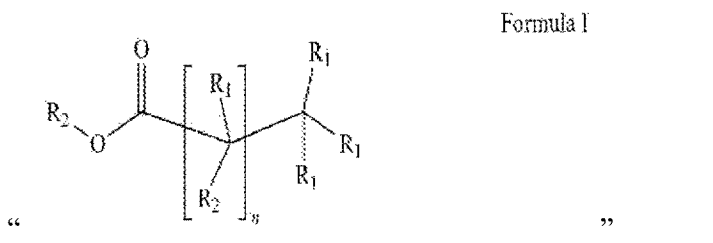

" Formula I "

And insert:

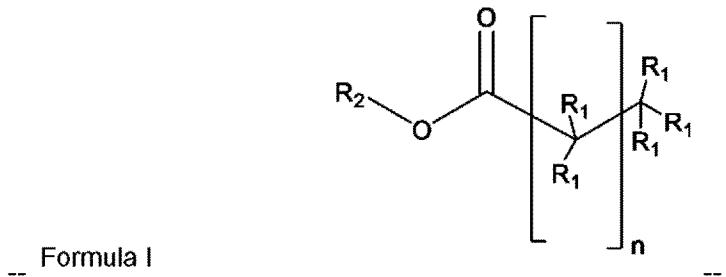

-- Formula I --

Column 29, Line 25, delete:

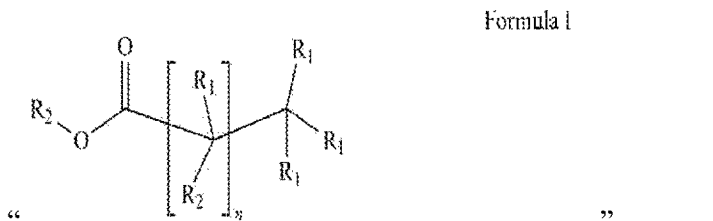

" Formula I "

And insert:

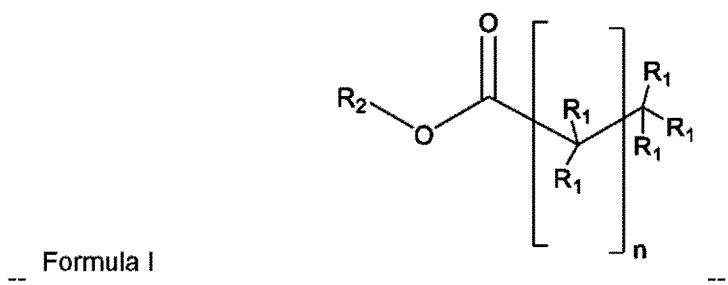

-- Formula I --